US005589563A

United States Patent [19]
Ward et al.

[11] Patent Number: 5,589,563
[45] Date of Patent: Dec. 31, 1996

[54] SURFACE-MODIFYING ENDGROUPS FOR BIOMEDICAL POLYMERS

[75] Inventors: Robert S. Ward, Lafayette; Kathleen A. White, Pleasant Hill, both of Calif.

[73] Assignee: The Polymer Technology Group, Calif.

[21] Appl. No.: 221,666

[22] Filed: Apr. 1, 1994

Related U.S. Application Data

[63] Continuation-in-part of Ser. No. 52,361, Apr. 23, 1993, Pat. No. 5,428,123, which is a continuation-in-part of Ser. No. 874,336, Apr. 24, 1992, abandoned.

[51] Int. Cl.$^6$ ................................................ C08G 18/00
[52] U.S. Cl. ............................ 528/44; 528/28; 528/25; 528/10; 528/34; 210/500.21; 210/500.23; 525/453; 525/459; 525/460
[58] Field of Search .................................. 528/44, 28, 25, 528/10, 34; 210/100.21, 500.23; 525/453, 459, 460

[56] References Cited

U.S. PATENT DOCUMENTS

| | | |
|---|---|---|
| 4,530,974 | 7/1985 | Munro et al. . |
| 4,663,413 | 5/1987 | Ward et al. . |
| 4,675,361 | 6/1987 | Ward, Jr. . |
| 4,686,137 | 8/1987 | Ward et al. . |
| 4,861,830 | 8/1989 | Ward, Jr. . |
| 4,963,595 | 10/1990 | Ward et al. . |
| 5,017,664 | 5/1991 | Grasel et al. . |
| 5,120,813 | 6/1992 | Ward, Jr. ................................ 528/28 |
| 5,235,003 | 8/1993 | Ward et al. . |

OTHER PUBLICATIONS

Farrar et al., "In Vivo Evaluations of a New Thromboresistant Polyurethane for Artificial Heart Blood Pumps", *J Thorac Cardiovasc Surgery*, 1988 (95), pp. 191–200.

Ward et al., "Use of Surface–Modifying Additives in the Development of a New Biomedical Polyurethaneurea", *Polyurethanes In Biomedical Engineering*, Elsevier Science Publishers, Amsterdam, 1984, pp. 181–200.

Ward, "Surface Modifying Additives for Biomedical Polymers", *IEEE Engineering in Medicine and Biology Magazine*, Jun. 1989, pp. 22–25.

Ward et al., "BPS–215M: A New Polyurethaneurea for Biomedical Devices: Development and in Vivo Testing in the Pierce–Donachy VAD", *Transactions 13th Annual Meeting of the Society for Biomaterials*, Jun. 1987.

Ward et al, "Use of Oligomeric End–Groups to Modify Surface Properties of Biomedical Polymers", *Transactions 20th Annual Meeting of the Society for Biomaterials*, Apr., 1994.

*Primary Examiner*—Shelley A. Dodson
*Assistant Examiner*—Duc Truong
*Attorney, Agent, or Firm*—Albert P. Halluin; Richard J. Gallagher; Pennie & Edmonds

[57] ABSTRACT

The present invention relates to novel polymeric compositions of matter and their use. Said polymeric compositions of matter are surface active endgroup-containing polymers that comprise a linear base polymer having covalently bonded surface active endgroups of a nature and present in an amount such that said polymers have a surface or interfacial tension that differs by at least 1 dyne/cm from the surface or interfacial tension of an otherwise identical polymer that does not contain said covalently bonded surface active endgroups. The novel linear polymers according to the present invention are particularly suitable for use in the manufacture of medical devices, and especially of medical devices intended to be used in contact with bodily fluids such as blood. Examples of such medical devices include catheters and artificial hearts.

51 Claims, 8 Drawing Sheets

SURFACE-MODIFYING ENDGROUPS FOR BIOMEDICAL POLYMERS

This application is a continuation-in-part of U.S. patent application Ser. No. 08/052,361, filed Apr. 23, 1993, now U.S. Pat. No. 5,428,123, which in turn is a continuation-in-part of U.S. patent application Ser. No. 07/874,336, filed Apr. 24, 1992, now abandoned. The disclosures of both said applications are expressly incorporated herein by reference.

FIELD OF THE INVENTION

The present invention relates to novel polymeric compositions of matter and their use. Said polymeric compositions of matter are linear block copolymers, preferably polyurethanes. The novel linear block copolymers according to the present invention are particularly suitable for use in the manufacture of medical devices, and especially of medical devices intended to be used in contact with bodily fluids such as blood. Examples of such medical devices include catheters and artificial hearts.

BACKGROUND OF THE INVENTION

Many synthetic polymers have characteristics that make them useful as biomedical materials. One reason for this is the wide range of properties available from man-made polymers, The chemistry of the repeat unit, the shape of the molecular backbone, and the existence and concentration of intermolecular bonds among the millions of molecules that make up the polymer sample all influence ultimate properties. Additional property variations are possible in polymers with more than one kind of repeating unit. Copolymers, terpolymers, and even multipolymers are possible in which the properties of more than one polymer type are combined to produce a unique material. The arrangement of the different repeat units in copolymers allows further property variations. The overall concentration of each monomer is also a major determinant of the properties of copolymers, but unless one monomer is used in great excess over the other, the resulting properties can be quite different from either homopolymer.

In graft and block copolymers, particularly when graft or block length is high, some of the properties of the two homopolymers are retained. For instance, a hard, high-melting block can by copolymerized with a soft rubbery block. With the proper arrangement of the blocks, the resulting copolymer can be a thermoplastic elastomer. At room temperature, the liquid-like soft blocks are strengthened and reinforced by the hard blocks or segments. At elevated temperatures, the hard blocks soften and flow to permit thermoplastic processing. Upon cooling, the original structure re-forms. The thermoplastic polyurethanes, which is an important class of biomaterials, have this block, or segmented, structure. Many interesting polymers can be made by combining one hard block with two or three different soft blocks. These polymers can have interesting permeability properties and biocompatibility, both of which can be tailored over a wide range by varying block chemistry and concentration.

In addition to the structural factors mentioned, the shape of a polymer's molecular weight distribution and its average molecular weight can have a significant effect on polymer properties. If one were to fractionate a typical polymer sample according to chain length, one might find that the low molecular weight homologues were waxes or even liquids, while the high molecular weight fractions were tough and viscous, even at elevated temperatures. The macroscopic properties that are measured and assigned to polymers are really the weighted averages of the properties of the various polymer fractions that are present in the sample.

Although the life-threatening consequences of inadequate biocompatibility in an artificial heart are well appreciated, lack of biocompatibility is seldom implicated when complications occur with simple acute devices such as vascular catheters. In fact, all blood and tissue contacting devices could probably benefit from improved biomaterials. Clotting, inflammatory response, and infection in even the simplest devices can result in sudden death of irreversible damage to the patient. The blood-materials interactions that occur at a smooth surface are affected only by the constitution of the outer few molecular monolayers of the polymer. This means that as long as the polymer does not contain any leachable impurities, the chemistry of the bulk polymer, which is distant from the biological interface, does not affect in vivo performance.

Many commercially available polymers contain additives or impurities that are surface-active. A surface-active agent, or surfactant, is capable of migrating to an interface and populating that interface at a concentration that is much higher than its average concentration in the bulk phase. Extremely surface-active materials can have nearly 100 percent concentration in a surface, even if their initial bulk or average concentration in the polymer is in the parts per million range. This is analogous to the effect a detergent has on the surface tension and surface chemistry of water. Accordingly, trying to interpret the surface analysis of a polymer contaminated with unknown substance is very difficult. In the absence of sensitive surface analysis, a sample's biological response may be wrongly assigned to the base polymer when it is, in fact, largely due to a contaminant. Processing or thermal history variations can lead to variability in in vivo performance if differences in the amounts of additive or impurity in the surface are produced.

Certain block and graft copolymers can add additional complexity to the relationship between surface chemistry and bulk chemistry. Solids and liquids try to minimize interfacial energy. This is the same driving force that causes low energy surface-active impurities to migrate to the air-facing surface of a polymer. Since air is a low-energy fluid, the interface between air and the polymer will have the lowest energy when the polymer surface also has a low energy. Migration of the surfactant to the polymer surface succeeds in lowering polymer surface energy and, therefore, overall interfacial energy. This effect is thought to minimize the activation of blood constituents for coagulation, cell adhesion, and other adverse biological processes.

In many block and graft copolymers, another mechanism for interfacial energy minimization exists. By reorientation of the surface molecular layers, one of the blocks or grafts can preferentially populate the surface. For instance, when brought to equilibrium in air, a block copolymer comprised of high surface energy hard segments and low surface energy soft segments will have a surface that is mostly comprised of the so-called soft block or low surface energy block. It is even possible that none of the more polar, hard segment will be present in the polymer surface. A polymer put into the blood stream is exposed to the more polar, aqueous environment of the blood. The polymer may then attempt to reorient its polar blocks toward the surface in order to minimize the energy of the blood-polymer interface.

Surface Modifying Additives

All biomedical polymer applications have requirements that can be divided into bulk property and surface property categories. An elastomer for an artificial heart, for instance, must have good bulk mechanical properties such as flex life, toughness, flexibility, and processability. This same polymer must also have a surface which does not cause blood to clot or the adjacent tissue to become inflamed.

In many classes of polymers, the relationship between the molecular variables and the bulk properties is fairly well understood. A systematic, if somewhat empirical, process may be used to achieve the desired bulk properties. In the case of surface properties, their relationship to the variables that can be manipulated by the materials scientist is less well known, and is clouded by the influence of the ever-present impurities. However, even if a precise functional relationship were known between surface properties and first-order molecular variables, another problem would still exist: the chances are remote that an optimum in both surface and bulk properties could be found at a single molecular structure and molecular weight.

This basic dilemma of biomaterials development has often led device manufacturers to use surface treatments or coatings applied after the device or component is fabricated. A method that is often more satisfactory involves a simple blending step before fabrication of the surface. This approach is described in detail in U.S. Pat. Nos. 4,663,413, 4,675,361, 4,861,830, 4,963,595, and 5,235,003, the disclosures of which are expressly incorporated herein by reference. The approach takes advantage of two mechanisms by which condensed phases of matter minimize their interfacial energy: the migration of species from the bulk to the surface and the reorientation of surface molecules.

The process begins with the synthesis of novel copolymers and terpolymers called surface-modifying additives or SMAs. A small amount of SMA is blended with the base polymer before device fabrication. During and after fabrication, the SMA migrates to the surface in high concentration. This dramatically changes the outermost molecular monolayers, which comprise the region which is believed to determine biocompatibility. The SMAs are relatively high molecular weight copolymers that are at least partially compatible with the base polymer. Both factors help the SMA to remain permanently anchored to the base polymer. As with many surfactants, so little of the SMA is required to achieve the desired change in surface chemistry that the original bulk properties are preserved.

Effective surface modifying additives are amphipathic in structure. That is, they have both polar and nonpolar blocks which may be connected by short hard block, allowing them to reorient as the environment changes. It is believed that the SMA's surface activity and polar/nonpolar structure are responsible for their ability to improve thromboresistance. Plasma proteins are present at high concentrations in the blood and readily adsorb onto polymer surfaces. The conformational changes in plasma proteins that occur upon adsorption have been implicated in surface-induced thrombosis. Thus, SMAs may improve thromboresistance by minimizing the interfacial energy between the blood and the polymer surface. The reduced energy gradient between the polymer surface and the protein's natural environment in the blood may reduce the tendency for the adsorbing proteins to change conformation and trigger events leading to thrombus formation.

The use of SMAs in the production of real biomedical devices is very simple. Before the device is made, the base polymer is blended with SMA and (re)formed into pellets. Alternatively, a base polymer dissolved in a solvent can have SMA added to it. After addition of the SMA, the base polymer is then processed (e.g., molded, extruded, or cast) in the usual way to make the device. The surface modification generally develops spontaneously, but surface migration may also be accelerated by storage at elevated temperature. Since no post-fabrication coatings or surface treatments are required, rejects from these operations are eliminated and incremental expense is minimized. The process is reproducible and can easily be monitored with simple contact angle measurements or other methods of surface analysis.

Surfactants contain both lyophobic and a lyophilic moieties. At the air interface the 'liquid-loving' lyophilic moiety faces the water while the lyophobic portion accumulates at the air side of the interface. A similar situation can occur in polymers with surface modifying additives (SMAS) even when the base polymer and SMA are solids at room temperature.

During and/or after fabrication of a formed article made from the admixture of the base polymer and the surface modifying additive (SMA) polymer, the surface 'develops' as the SMA diffuses from the bulk to the surface region. This process occurs rapidly when fabrication methods are used which involve the slow conversion of the polymer blend from a liquid to a solid (due to the faster diffusion rate of the SMA in the liquid compared to the solid base polymer). One example of a fabrication processes in which the transition from liquid to solid is fairly slow includes solvent-based operations such as dipping, spraying, casting and the like, during which solvent evaporates from the polymer solution leaving a solid layer behind. Another example includes evaporation of water from a water-based emulsion of polymer to leave a coalesced film of polymer. A third example includes slow curing of a 100% solids liquid polymer system into a solid configured article.

The rate of surface development generally occurs more slowly when the conversion process rapidly converts the liquid polymer to a solid such as when a molten polymer is extruded and rapidly solidified by immersion in water or by cooling in an air stream. Perhaps the slowest rate of surface development occurs when the fabrication process exposes new surface area on a solid preform of the polymer blend, such as in the case on machining a part on a lathe or other machine tool. In all methods of fabrication the rate of surface development can be accelerated by applying heat to hasten the rate of diffusion of the SMA to the surface of the formed article, e.g. by annealing at elevated temperatures. By using an annealing temperature above the glass transition temperature (Tg) of an amorphous or semicrystalline polymer, or by annealing at a temperature near or above the melting point (Tm) of a crystalline polymer, the rate of surface development can be significantly increased.

In addition to increasing ambient temperature, other methods of increasing the molecular mobility of the base polymer will also hasten the process of surface development of a base polymer/SMA blend. The incorporation of a plasticizer or solvent which lowers the glass transition temperature of the base polymer is one example. Making structural changes to the base polymer during its synthesis to reduce base polymer cohesive energy density, e.g. through the incorporation of bulky side chains is another method. Similarly, any process which reduces the base polymer dominant thermal transition temperature to lower than ambient temperature will hasten surface development at that ambient temperature.

The process of surface development is an approach to equilibrium which can involve the diffusion of the SMA polymer to the surface of the formed article and/or (re)orientation of the SMA at the surface of the formed article. The process of surface development is driven by the tendency of all condensed phases of matter to minimize their interfacial energy. The minimum interfacial energy per unit area of the interface occurs when the chemical groups (and their packing density) is identical in the two surfaces which comprise the interface. Since the nature of the interface changes as the polymer surface is exposed to different environments, the minimization of interfacial energy can involve a surface excess of the SMA in one environment and a surface deficiency of the SMA in another. A material's surface energy is actually its interfacial energy in contact with air. If a silicone-containing SMA polymer is added to a base polymer whose surface energy is higher than that of the silicone SMA, the silicone will eventually migrate to the air-interface of the formed article. The surface migration of the SMA is driven by the fact that its presence in the surface layer reduces the interfacial energy of the surface in contact with air (air is a low-surface-energy fluid) by reducing the polymer's surface energy. On the other hand, if after equilibration in air the same surface is immersed in water (a high-surface-energy fluid) the minimization of interfacial energy will require a surface deficiency of the SMA at the interface. This can occur if the base polymer replaces the SMA in the surface layer of the polymer (blend). For most base polymers this change does not bring interfacial energy to zero, but it does reduce interfacial energy relative to the case in which a silicone-rich surface faces the water.

If the silicone-containing SMA polymer also contains additional chemical chains which are higher in surface energy than the base polymer, the SMA can be even more effective in minimizing interfacial energy in a variety of environments. The presence of both hydrophobic and hydrophilic moieties on the same molecule constitutes a so-called amphipathic structure. A silicone-containing copolymer which also contains polyethyleneoxide chains is an example of an amphipathic molecule. Upon immersion in water, for example, a surface previously equilibrated in air can minimize its surface energy, not by replacement of the surface SMA with bulk polymer, but by the reorientation of the SMA so that it presents its high energy (hydrophilic) groups to the water.

The ability of a surface to minimize its interfacial energy is apparently an important determinant of biocompatibility. Blood compatibility of a medical device, in particular, is improved when its surface, layer can reorient to minimize interfacial energy in contact with blood. This may involve the minimization of denaturation of plasma proteins which are involved in the clotting cascade, since they are exposed to a lower energy gradient when they adsorb on the'surface. It may also involve the selective adsorption of certain blood proteins in the blood-contacting surface, which proteins (e.g. albumin) may have a passivating effect on the surface.

As disclosed in U.S. patent applications Ser. Nos. 08/052, 361, filed Apr. 23, 1993, and 07/874,336, filed Apr. 24, 1992, the disclosures of both of which applications being expressly incorporated herein by reference, high molecular weight, film-forming polymers have been used as surface modifying additives in a variety of base polymers. In these applications, SMAs were synthesized to have an amphipathic structure (e.g. as silicone-containing polyurethanes or silicone-polyethyleneoxide-containing polyurethanes) and the synthesized polymer was used as a minor additive in a base polymer. Typically the blend of SMA and base polymer would contain ≦5% by weight SMA with the balance made up of the base polymer. Once the blend of the two polymers is fabricated into a configured article the surface develops by diffusion of the SMA to the surface of the configured article, and its orientation in the surface layer. In this way the outer few Ångstroms of the configured article attain a surface chemistry dominated by the SMA, and bulk properties are dominated by the base polymer. This is an effective way of obtaining a polymer (blend) with simultaneously optimized surface and bulk properties.

Although SMA-modified base polymers are presently in clinical use in successful medical devices, the approach has some shortcomings. The rate of approach to equilibrium surface composition can be very slow at temperatures at which the polymer's continuous phase is glassy or crystalline. This requires elevated temperature and/or long storage times to completely affect the surface modification. In material applications involving abrasion or erosion of the surface it is not clear how the surface layer can be replenished by the bulk SMA 'reservoir', particularly if the use temperature is below Tg or Tm of the polymer's continuous phase. The use of SMAs requires a separate synthesis step which is often followed by recovery and purification operations and quality assurance testing. Care must also be taken to remove or avoid low molecular weight homologues in the SMA polymer which can potentially migrate from the base polymer SMA blend during use. Furthermore in many applications it is desirable to have the surface modification be a 'permanent part' of the base polymer.

The use of the polymeric SMA as a minor ingredient in the blend has some disadvantages. In manufacturing methods which involve dipping a mandrel in a solution or liquid form of the polymer blend the SMA can be selectively removed from the dipping bath. This happens because a Langmuir-Blodgett film deposits on the mandrel. The surface of the dipping bath is enriched in the SMA due to its surface-active nature. As the mandrel is removed from the dipping bath the film which is deposited on the mandrel comes largely from the surface layer of the bath. Consequently the average concentration of SMA polymer deposited on the mandrel is higher than the average or bulk concentration of the SMA in the base polymer.

Several investigators have proposed the modification of fully-reacted base polymers (e.g. polyurethanes) via the grafting of side chain structures, e.g. with sulphonated alkyl groups, In this approach urethane or urea groups in the hard segments are used as reactive sites for grafting. In general, the use of the hard segment groups for grafting weakens the base polymer by discouraging hard-segment/hard-segment interactions.

SUMMARY OF THE INVENTION

In order to overcome some of the limitations of SMAs, the present invention provides a series of (biomedical) base polymers that have SMA-like properties "built in" and which do not rely on the use of additives to achieve the desired surface chemistry. This has been accomplished through the use of surface-active endgroups having a range of chemical structures and/or optional functional groups. By restricting the surface-modifying moieties to the termini of linear or branched base polymers, changes to the base polymer's bulk properties are minimized. The added mobility of endgroups relative to backbone groups is thought to facilitate the formation of uniform overlayers by the surface-active (end) blocks. The fact that essentially all polymer chains carry the surface-modifying moiety eliminates many of the potential problems associated with additives.

In contrast to the grafting approach mentioned above, polyurethanes prepared according to the present invention couple endgroups to the backbone polymer during synthesis, via a terminal isocyanate group, not via a hard segment. The use of the surface active endgroups, therefore, leaves the original polymer backbone intact so the polymer retains strength and processability.

Surface modification via surface active endgroups (SME) is readily adapted to the synthesis of polymers that normally incorporate a low molecular weight monofunctional endgroups for molecular weight control. The use of dodecylamine in place of diethylamine in the synthesis of segmented polyurethaneureas is one example. Using this approach, polymers have been made with tensile strengths exceeding 5000 psi which contain=0.5 wt. % dodecyl groups. With higher molecular weight endgroups, total endgroup concentration can be much higher. Using monofunctional 2000-MW polydimethylsiloxane-amine (MPSX), high-strength elastomers have been prepared with nominal 6% (wt./wt.) siloxane content. Using monofunctional polyethyleneoxide-amines or alcohols, up to 16% ethyleneoxide has been incorporated into otherwise hydrophobic polymers, with good strength retention.

In addition to the use of a single endgroup chemistry, the SME approach allows mixed endgroups to be present in a single polymer. The use of hydrophobic and hydrophilic endgroups gives amphipathic structures in which the hydrophobic/hydrophilic balance may be easily varied.

Suitable surface active reagents are readily available, and the synthesis procedure is quite straightforward. The use of surface-modifying endgroups according to the present invention provides for the development and manufacture of a wide range of new biomaterials.

DESCRIPTION OF THE PREFERRED EMBODIMENTS

Figure 1:
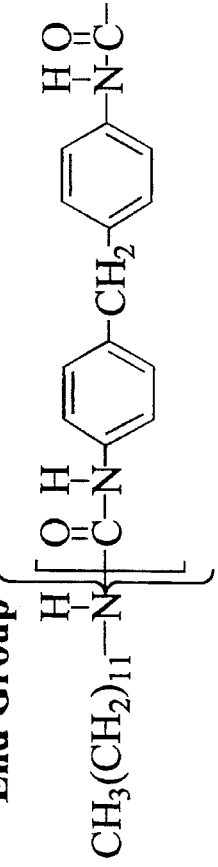
FIG. 1 depicts the structure of a typical polymer having PTMO soft segments prepared by means of solution-based synthesis according to the present invention.
Figure 1:
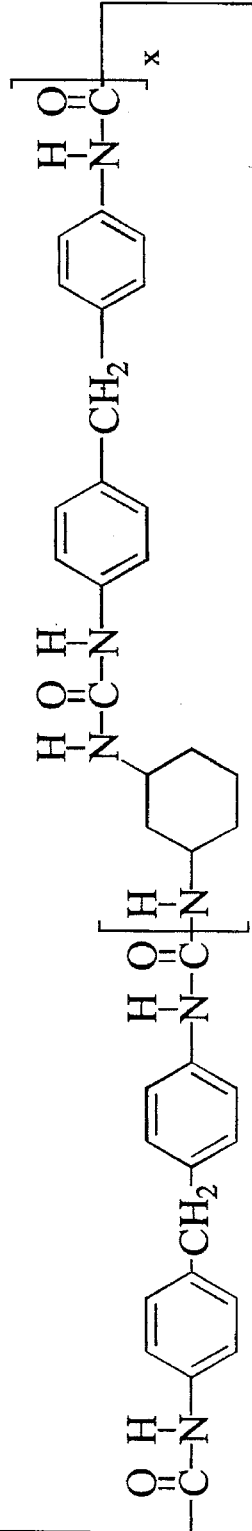
Figure 1:
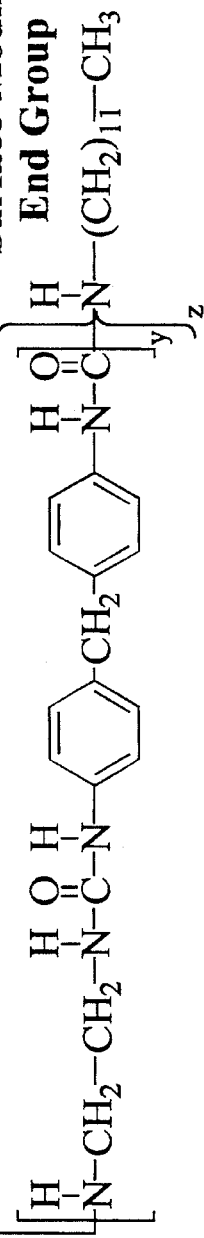

The present invention provides surface active endgroup-containing polymers that comprise linear base polymers in which the endgroups contain covalently bonded surface active groups such that the surface activity of said polymers is controlled by said surface active groups. Said surface active groups include not only the relatively low molecular weight polymers that are traditionally referred to as oligomers but also other organic moieties having surface active properties, such as alkyl groups containing from 8 through 30 carbon atoms, e.g. as derived from dodecylamine. The terminology "linear" in this context refers to polymers that are capable of spacial alignments in which one or both "ends" can move relative to the main body of the polymer in such a way that they can present themselves at the interface of a sample of such polymer with a different substance. The terminology "controlled by said surface active groups" in this context means that the surface activity of a sample of a polymer according to the invention reflects the surface activity of said endgroups rather than of the base polymer. Where the surface active endgroups are all identical or similar, the surface activity will generally be classifiable as hydrophobic or hydrophilic. However, where mixed endgroups are present in a single polymer, more complex surface activity may be achieved. For instance, the use of both hydrophobic and hydrophilic endgroups in the same polymeric structure gives amphipathic structures in which, depending upon the qualitative and quantitative parameters selected, the hydrophobic/hydrophilic balance may be varied to obtain a range of desired surface activity in a single polymer.

The benefits to be derived from surface modification according to the present invention vary widely depending on the chemistry and molecular weight of the endgroups employed, the nature of the base polymer to which the surface modifying endgroups have been appended, and the ultimate use of the polymer. The use of SMEs to increase biocompatibility has already been discussed together with a possible explanation relating to reduced protein denaturation upon adsorption to the surface and/or the selective in situ adsorption of 'passivating' proteins from blood or tissue.

A related use of SMEs is the improvement of biostability of polymers which are implanted in humans or animals. Biostability, the converse of biodegradability, refers to the polymer's ability to withstand degradation in the harsh environment of the body. Such degradation (which can involve crosslinking/embrittlement and/or chain scission/softening of the polymer) generally begins at the surface of the implanted device or prosthesis and subsequently affects the bulk material below the surface. Severe degradation can result in device failure and may be life-threatening in many applications, e.g. in a prosthetic heart valve, vascular graft, or cardiac-assist device.

Since SMEs profoundly affect the surface or interfacial layer of a formed article (such as an implanted device or prosthesis) the SME may be used to enhance the biostability of a base polymer by providing a more biostable interface to the body. An example of this application of SMEs is in the use of biostabilizing endgroups on a polyurethane or other block or segmented copolymer. The base polymer is chosen for its initial bulk properties such as tensile strength, flex life, modulus, etc. The SME is chosen to give the desired surface properties e.g. hydrophobicity, resistance to hydrolytic degradation, resistance to oxidation, and/or resistance to other modes of degradation.

It has been found that polydimethylsiloxane and similar polydialkylsiloxanes degrade in the body very slowly. The little degradation that does occur is often dominated by crosslinking of the polymer (as evidenced by decreased solubility in solvents following implantation) rather than by molecular weight reduction via chain scission. Many segmented or block copolymers of interest as biomaterials appear to degrade primarily by chain scission as measured by reduced GPC molecular weights following implantation.

In addition to degrading by crosslinking, many silicones are hydrophobic and water-repellent. When present in the surface of a base polymer they may thereby protect the base polymer from hydrolytic degradation by the aqueous fluids within the body. Similarly many silicones are resistant to oxidative degradation. A surface layer of silicone may therefore be expected to protect the underlying base polymer from oxidative degradation as well. The tendency of the silicone to degrade by crosslinking may also have a synergistic protective effect on the base polymer if the base polymer's main mode of degradation is chain scission. Degradation products of the silicone endgroups, e.g. free radicals, may chemically combine with degradation products of the base polymer. Thus the chain scission of the base polymer may be counteracted by the crosslinking of the (silicone) endgroups, the net result being a preservation of molecular weight and morphology that would be absent if either moiety was not present.

While not wanting to be limited by theory it can be seen that surface modifying endgroups can have many desirable effects on the base polymer to which they are appended. Virtually any surface-related property may be modified and/or enhanced by SME including: surface chemical composition, coefficient of friction, abrasion resistance, resistance to environmental degradation, wettability and adhesion, or alternatively release properties, printability, chemical reactivity, catalytic properties, adsorption properties, dyeability, color, thrombogenicity, tissue compatibility, inflammatory response of implants, tissue ingrowth/encapsulation of implants, optical properties, etc.

In addition to surface property enhancement, it is also possible to use SMEs to enhance properties that are often considered to be bulk properties of polymers. This is particularly true when the so-called bulk property is effected by the constitution of the surface layers of the formed article. The permeability of a nonporous polymer film or membrane, for example, is the product of the diffusivity and the solubility of the permeating species in the polymer. The permeant must first dissolve in the surface of the membrane or film and then, while dissolved, diffuse through it and desorb on the opposite side. An SME can discourage permeation by presenting a surface layer that has low solubility to a permeant. For example, a fluorocarbon or silicone SME might reduce moisture vapor permeation in a base polymer due to surface hydrophobicity. Conversely an SME based on a water soluble oligomer such as poly(ethylene oxide) or polyvinyl alcohol might improve water vapor permeability by presenting a hydrophilic surface. Note that in both cases any SME not residing in the surface of the formed article must be present in the bulk.

Depending on their overall bulk concentration in the modified polymer, the SMEs can have an effect on the bulk properties of the base polymer. In some applications the SME's effect on base polymer bulk properties may be desirable. In other applications it may need to be minimized. In the event that a bulk property modification is to be maximized, the molecular weight of the SME should be maximized in proportion to the molecular weight of the base polymer. This will raise the total weight and volume fraction of (oligomeric) endgroups in the modified polymer. In most cases the effect on the bulk properties of the base polymer is to be minimized and it is best to minimize the molecular weight of the endgroups in relation to the molecular weight of the base polymer. However, too low an endgroup molecular weight may destroy the surface modifying effect of the endgroups. In general, higher molecular weight endgroups will be more surface active in the base polymer and will be able to assemble/orient in the surface to produce more complete coverage of the surface than lower molecular weight endgroup homologues.

The optimum end-group-to-base-polymer molecular weight ratio for a given application can be determined empirically by applying the appropriate surface-sensitive and bulk-sensitive characterization methods to various candidate end-group-modified polymers. Suitable bulk characterization methods are well known to those skilled in the art and include tensile testing, thermal analysis, dynamic mechanical testing, indentation hardness, melt rheology, permeability testing, and a variety of other methods. Suitable surface-sensitive characterization methods which probe, the chemical constitution of surfaces include contact angle and wettability measurements, low take-off-angle electron spectroscopy for chemical analysis (ESCA), attenuated total reflection infrared spectroscopy, secondary ion mass spectrometry (SIMS), and techniques for visualizing surfaces such as scanning tunneling microscopy. It must be kept in mind, however, that most surface-sensitive analytical methods probe to a certain depth below the surface. The more surface-sensitive the method the more revealing the analysis will be. This is true because SMEs are likely to affect surface composition in a region encompassing only a few monolayers below (and including) the surface molecular layer. An analytical method that integrates the information from the surface layer with chemical identity information from significant depth below the surface may 'miss' the dramatic change in surface chemical composition affected by the SME. It has been found that contact angle/wettability measurements and low takeoff-angle ESCA are suitably surface-sensitive to assess the effects of SMEs on surface chemistry.

An alternative to the use of surface chemical analysis to determine the effect of SMEs is to perform functional testing on the modified surface. Thrombogenicity, for example, could be measured directly, as a function SME molecular weight and chemistry to optimize an SME intended to improve blood compatibility of a base polymer. Similar functional testing can be applied to other surface properties, e.g. coefficient of friction. In this way the SME can be tailored to specific applications.

In an option employing surface chemical analysis and/or functional testing of the surface, various bulk characterization methods including those listed above can determine the effect of the SME on the bulk properties of the modified base polymer. The combination of bulk and surface property characterization will then direct the optimization which may involve an iterative process of synthesis and characterization until the desired balance of surface and bulk properties are achieved.

Preferred linear base polymers according to the present invention are biocompatible segmented block polyurethane copolymers comprising hard and soft segments. The hard segment of the copolymer of the invention may preferably have a molecular weight of about 160 to 10,000, and more preferably about 200 to 2,000. The molecular weight of the soft segment is typically about 200 to 1,000,000, and preferably about 400 to 9000.

In the development of the polyurethane copolymers of the invention, the elastomers are designed to have excellent physical characteristics, such as toughness and elongation.

In addition, the copolymers of this invention are designed as a family of materials with a broad range of modulus and hardness that may be tailored for many particular applications. Although tailoring of permeability properties of the copolymer of this invention is often of primary importance, within the structural constraints of the required permeability, it is also possible to tailor physical properties as well. In most cases the polymers of the present invention will have the desired protein and/or macromolecular permeability and also possess excellent physical properties as demonstrated by the following table, in which MDI is diphenylmethanediisocyanate, PTMO is polytetramethyleneoxide, MPSX is monofunctional hydroxy-terminated polydimethylsiloxane, and MPEO is monofunctional hydroxy-terminated poly(ethylene oxide):

| Hard Seg. | Soft Segment | Endgroup | Tensile Str. (psi) | Ult. Elong. (%) | Init. Mod. (psi) |
| --- | --- | --- | --- | --- | --- |
| MDI | PTMO | Dodecyl | 6529 ± 391 | 926 ± 62 | 828 ± 118 |
| MDI | PTMO | MPSX | 5397 ± 267 | 926 ± 8 | 610 ± 24 |
| MDI | Carbonate | MPSX | 6005 ± 442 | 628 ± 16 | 852 ± 72 |
| MDI | Mixed | MPSX + MPEO | 4200 | 1200 | 1500 |

The fact that excellent physical properties can be obtained is of particular importance in maintaining barrier properties of the membranes, i.e., exclusion of unwanted cells and high molecular weight permeants. A high level of toughness when compared to certain gels and hydrocolloids permits the copolymers of the present invention to be fabricated into many useful shapes while still maintaining physical integrity of the membrane. Some typical physical properties of membranes of the present invention are as follows: tensile strength greater than 350 psi; elongation at break greater than 300%; initial modulus about 75 to 20,000 psi.

Because of an interest in preparing polyurethanes of different moduli, the relationship between modulus and total hard segment content is sometimes important. For the polyurethanes of the present invention, the hard segment content is defined herein as the weight of diisocyanate plus chain extender, divided by total polymer weight. A linear proportion is found between initial, i.e., measured at less than 10% strain, modulus and hard segment over a range of about 9 to 30% hard segment content. Linear, not crosslinked, elastomers of about 9% hard segment and below have properties similar to unvulcanized rubber and are, therefore, not of particular interest for the present use as unsupported films or membranes. They may be used, however, as coatings or impregnations on porous reinforcing substrates. At high elongations, the pure soft segment may undergo reversible crystallization, giving an increased modulus and a somewhat reduced ultimate elongation. The thus resulting polymer also possesses excellent strength and certain other desirable properties.

The Polyisocyanates

Preferred polyisocyanates for the preparation of the hard segment of the copolymer of the invention are aromatic or aliphatic diisocyanates. The diisocyanates may be selected from the group consisting of alkyl diisocyanates, arylalkyl diisocyanates, cycloalkylalkyl diisocyanates, alkylaryl diisocyanates, cycloalkyl diisocyanates, aryl diisocyanates, cycloalkylaryl diisocyanates, all of which may be further substituted with oxygen, and mixtures thereof. Examples of suitable diisocyanates include 4,4'-diphenylmethanediisocyanate, hexamethylenediisocyanate, dicyclohexylmethanediisocyanate, 2,4-toluenediisocyanate, 2,6-toluenediisocyanate, hexamethylene-1,6-diisocyanate, tetramethylene-1,4-diisocyanate, cyclohexane-1,4-diisocyanate, naphthalene-1,5-diisocyanate, diphenylmethane-4,4'-diisocyanate, xylylenediisocyanate, dicyclohexylmethane-4,4'-diisocyanate, 1,4-benzene diisocyanate, 3,3'-dimethoxy-4,4'-diphenyldiisocyanate, m-phenylenediisocyanate, isophoronediisocyanate, polymethylenepolyphenyldiisocyanate, 4,4'-biphenylenediisocyanate, 4-isocyanatocyclohexyl-4'-isocyanate, and mixtures thereof. Preferred are diphenylmethanediisocyanate (MDI), dicyclohexylmethanediisocyanate, and mixtures thereof. The molecular weight of the diisocyanate component of the hard segment will preferably be from 100–500 and more preferably from 150–270.

The chain extender of the hard segment used in the preparation of the copolymers of the invention may be an aliphatic polyol or an aliphatic or aromatic polyamine such as those known for preparing polyurethanes. The molecular weight of the chain extender component of the hard segment will preferably be from 18–500 and more preferably from 60–200.

The polyol for the hard segment may be preferably selected from the group consisting of alkylene, cycloalkylene, and arylene diols, triols, tetraalcohols, and pentaalcohols, and mixtures thereof. Examples of polyols suitable for the preparation of the hard segment are 1,4-butanediol, ethylene glycol, 1,6-hexanediol, glycerine, trimethylolpropane, pentaerythritol, 1,4-cyclohexane dimethanol, phenyldiethanolamine, and mixtures thereof, among others. However, other polyols are also suitable.

The polyamine of the hard segment may be selected from the group consisting of alkyl, cycloalkyl, and aryl amines which may be further substituted with nitrogen, oxygen, or halogen, complexes thereof with alkali metal salts, and mixtures thereof. Suitable polyamines for preparing the hard segment are p,p'-methylenedianiline and complexes thereof with alkali metal chlorides, bromides, iodides, nitrites, and nitrates, 4,4'-methylene-bis(2-chloroaniline), piperazine, 2-methylpiperazine, oxydianiline, hydrazine, ethylenediamine, cyclohexanediamine, xylylenediamine, bis(p-aminocyclohexyl)methane, the dimethyl ester of 4,4'-methylenedianthranilic acid, p-phenylenediamine, o-phenylenediamine, 4,4'-methylenebis(2-methoxyaniline), 4,4'-methylenebis(N-methylaniline), 2,4-toluenediamine, 2,6-toluenediamine, benzidine, dichlorobenzidine, 3,3'-dimethylbenzidine, 3,3'-dimethoxybenzidine, diansidine, 1,3-propanediol bis(p-aminobenzoate), isophorone diamine, and mixtures thereof. Particularly convenient polyamine mixtures are of ethylenediamine and 1,3-cyclohexanediamine.

The Polyols

The soft segment used in the preparation of the polyurethane of the invention may be a polyfunctional aliphatic polyol, or a polyfunctional aliphatic or aromatic amine, such as are commonly used for the preparation of polyurethanes or mixtures thereof.

The aliphatic polyols of the soft segment may be selected from the group consisting of linear and branched polyalkylene and polyalkenyl oxides, random and block copolymers thereof, polycarbonate polyols, hydroxyl-terminated silicones, random and block copolymers thereof with polyalkylene oxides, linear and branched polyalkenyl and polyalkylene polyols, and mixtures thereof. However, other polyols may also be utilized if the resultant polymer possesses the required bulk properties, e.g. tensile strength. Examples of polyols that are suitable for use in the present invention are polyethylene oxides, polypropyleneoxides, polytetramethylene oxides (PTMO), random or block polypropylene oxide-polyethylene oxide copolymers, various ethyleneoxide-terminated polyols, random or block polytetramethylene oxide-polyethylene oxide copolymers, polycarbonate diols and triols, multifunctional hydroxyalkyl- or amine-terminated silicones, random or block silicone-polyethyleneoxide copolymers, polybutadiene diols and triols, polyisobutylene diols and triols, polybutylene oxide diols and triols, and mixtures thereof.

The amines of the soft segment may be selected from the group consisting of amine-terminated homologues of the exemplary polyols, including but not limited to polyamine-terminated alkylene oxides and random and block copolymers thereof, polyamine-terminated silicones, random and block copolymers thereof with polyalkylene oxides and mixtures thereof. Examples of the amines that are suitable for use in the present invention are multifunctional amine-terminated polytetramethylene oxides, multifunctional amine terminated polyethylene oxides, random or block multifunctional amine terminated polypropylene oxide-polyethylene oxide copolymers, random or block multifunctional amine-terminated polytetramethylene oxide-polyethylene oxide copolymers, multifunctional amine-terminated silicones, random or block amine-terminated silicon polyethylene oxide copolymers and mixtures thereof.

The Endgroups

The surface active endgroups according to the present invention are introduced into polymers by means of a reaction that results in the formation of a covalent bond between the surface active moiety and the base polymer. When the base polymer is a polyurethane or other isocyanate-derived polymer, terminal isocyanate groups can conveniently be reacted with appropriate precursors that contain the surface active moiety. While such endgroup precursors are illustrated herein by alcohols and amines, any compound that contains an active hydrogen can be used to introduce the surface active moiety into the polymer. For instance, most compounds that contain a hydrogen atom bonded to oxygen react with isocyanate under proper conditions, including e.g. phenols. Essentially all compounds containing a hydrogen attached to a nitrogen are reactive, including e.g. amides. Carboxylic acids react with isocyanates; stearic acid could be used to introduce surface active endgroups into a polymer in accordance with the present invention. Sulfur compounds react in the same manner as their oxygen analogues, although at a much slower rate. Any method of that results in the formation of a covalent bond between the surface active moiety and the base polymer is thus contemplated according to the present invention.

Physicochemical Requirements of SMEs

The utility of SMEs is based on their ability to accumulate at the surface of a formed article made from the SME polymer. Such accumulation is driven by the minimization of interfacial energy of the system which occurs as a result of it. It is implicit in the use of SMEs that their chemical structure be different than the chemistry of the original endgroups of the base polymer to which they are appended. The use of a surface-modifying endgroup with chemical structure and molecular weight virtually identical to that of one or more end blocks or segments of a base polymer has little utility: no significant change in surface chemistry will result if such an SME accumulates in the surface. However, this is not the case relative to segments or blocks of the base polymer which lie within the backbone and which are therefore covalently bonded at more than one point to the base polymer. Polymer chain ends have more degrees of freedom of motion than chemically identical chains bonded at two or more points within the backbone of a base polymer. The added freedom of motion of the chain ends favors surface activity and the formation of molecular overlayers produced by chain folding and alignment/packing of adjacent chains to form monolayers. Thus there can be utility in appending SMEs to base polymers in which the SME chemistry/molecular weight is similar to that of one of the midblocks or midsegments of the base polymer.

For example, the use of an aromatic polycarbonate SME on a base polymer of structure BCB, in which B is aromatic polycarbonate and C is polydimethylsiloxane, would probably have little utility in terms of surface modification. However, the use of a polydimethylsiloxane SME on the same polymer could provide a more silicone-like surface chemistry to the SME-polymer (which would then have the structure, CBCBC). This is particularly true when the midblock (polydimethylsiloxane in this case) is of low molecular weight relative to the original end blocks of the base polymer, or if it is of low molecular weight relative to the SMEs of identical chemistry.

Selection of SMEs

Generally the utility of candidate SMEs for use with a specific base polymer can be judged by considering the original structure of the base polymer and the functional performance of the SME-modified polymer together with the environment in which the SME-modified polymer will function.

IN AIR: When the working environment of the SME-modified polymer is primarily air at low relative humidity, it is generally true that the most useful surface-modifying endgroups will give the modified base polymer a reduced solid surface tension or critical surface tension. That is, the useful SMEs will be of lower solid surface tension than the surface tension of the unmodified base polymer. This difference in surface tension can be measured by the well-known method of contact angle measurements on the surfaces of interest using sessile droplets of two pure solvent (e.g. water and methylene iodide). Application of the harmonic mean or geometric mean equation is used to determine the solid's surface tension based on the angle of contact between the liquid droplets and the surface, and the known liquid surface tensions of the two liquids. A difference of about 1 to 2 or more dyne/cm (ergs/sqcm) is significant. That degree of difference is generally sufficient to drive the SME to the surface and for benefit to be derived from the presence of the SME in the surface of the modified polymer. It is even more preferable when the difference in solid surface tension between the SME-modified polymer and the original base polymer is 5 or more dyne/cm.

IN LIQUIDS: In some SME-modified base polymers, the effect of the SME on solid surface tension, relative to the unmodified base polymer, may be minimal even if the SME dramatically alters the contact angle of a sessile drop of a single pure solvent, e.g. water. Since many functional surface properties are related to the wetting and spreading of specific liquids on the modified surface, the use of contact angle itself, rather than quantities derived from contact angle data, is often useful. A difference of about 2 to 5 or more degrees is significant. That degree of difference is generally sufficient to drive the SME to the surface and for benefit to be derived from the presence of the SME in the surface of the modified polymer. It is even more preferable when the difference in contact angle between the SME-modified polymer and the original base polymer is 5 or more degrees. A particularly useful case, in certain applications requiring liquid repellency by the surface, occurs when the SME causes the liquid to exhibit an advancing angle on the modified surface that is greater than 90 degrees (nonwetting) when the contact angle on the unmodified base polymer is less than 90 degrees (wetting). Another particularly useful case, in certain applications requiring enhanced wetting of the surface by the liquid occurs when the SME causes the liquid to exhibit an advancing angle on the modified surface that is less than 90 degrees (wetting) when the contact angle on the unmodified base polymer is greater than 90 degrees (nonwetting).

Some examples of significant modification of (water) contact angle by surface-modifying endgroups are shown in the following table. Polymer a., the PTMO-PUU control, is a polyetherurethane with a Polytetramethyleneoxide soft segment and a hard segment of diphenylmethane diisocyanate and mixed diamines (ethylenediamine and 1,3-cyclohexanediamine). Polymers b. through e. are the same base polymer with the SMEs appended as shown. Although water is used as the liquid in this example, similar benefit may be obtained in applications involving other liquids, e.g. oils.

| PTMO-PUU Polymer | SME | SME Mol. Wt. | Advancing Water-Contact Angle (°) |
|---|---|---|---|
| a. | none | NA | 84 ± 4.3 |
| b. | Dodecyl | — | 92 ± 2.8 |
| c. | Polydimethyl siloxane | 2000 | 93 ± 1.9 |
| d. | Fluorocarbon | low (mixed telomers) | 93 ± 2.2 |
| e. | Octadecyl | — | 110 ± 4.0 |

When the working environment of the SME-modified polymer involves immersion in a fluid of higher surface tension such as water or body fluids it is often true that the most useful surface modifying endgroups will be those which have a higher surface energy than the unmodified base polymer. In other cases, however, it may be of interest to actually increase the solid-fluid interfacial tension, e.g. for water repellency. In judging the effectiveness of SME it is therefore often useful to measure the effect of the SME on the interfacial tension of the surfaces in the fluid of interest, e.g. water. This can be done using the above contact angle methods and the appropriate equations. An SME capable of changing the interfacial tension of the surface in the fluid of interest by greater than about 1 to 2 dyne/cm (ergs/sqcm) is significant. Again, that degree of difference is generally sufficient to drive the SME to the surface and for benefit to be derived from the presence of the SME in the surface of the modified polymer. In this case, too, it is even more preferable when the difference in interfacial tension between the SME-modified polymer and the original base polymer is 5 or more dyne/cm.

IN BOTH AIR AND LIQUIDS: In some applications of SMEs, it is desirable to maximize the ability of the modified surface to minimize interfacial energy in a variety of environments. One example is the modification of a fiber-forming polymer for textiles such that in air the fibers present a low-energy soil-repelling surface (e.g. of silicone or fluorocarbon) but in water they present a higher-energy surface easily wetted by water and detergent solutions. The ability of a surface to quickly modify its chemical composition (e.g. through exchange of one type of group for another) as its environment changes can be measured by the well-known method of contact angle hysteresis. Here the so-called advancing contact angle of a liquid such as water is compared to its receding contact angle of the sessile droplet as it is retracted over the same surface. On a smooth surface the difference between advancing and receding angles, often expressed as a per cent of the advancing angle, is a measure of contact angle hysteresis: the ability of the surface to minimize interfacial energy. An SME capable of changing the contact angle hysteresis of the surface against the fluid of interest by greater than about 5% is significant. That degree of difference is generally sufficient to drive the SME to the surface and for benefit to be derived from the presence of the SME in the surface of the modified polymer. It is even more preferable when the difference in contact angle hysteresis between the SME-modified polymer the original base polymer is 10% or more. A particularly useful case in certain applications occurs when the SME causes the liquid to exhibit an advancing angle on the modified surface that is greater than 90 degrees (nonwetting) and a receding contact angle of less than 90 degrees (wetting).

Preferred monofunctional aliphatic polyols for the endgroup are monofunctional polyalkylene oxides, siloxanes, and mixtures or copolymers thereof. Examples of aliphatic polyols are monofunctional polyethylene oxides, monofunctional polytetramethylene oxides, monofunctional polypropylene oxides, monofunctional siloxanes, and mixtures and/or copolymers thereof. However, others are also suitable, so long as they serve to modify the surface activity of the polymer to which they are attached without substantially affecting its primary properties such as strength, bio-inertness, and so on.

The monofunctional amines of the endgroup may be selected from the group consisting of dialkylamines, amine-functional siloxanes, amine-terminated polyalkylene oxides, and mixtures and copolymers thereof.

In a preferred embodiment of the present invention, the block copolymer is a polyurethaneurea and the surface active endgroup is selected from the group consisting of monofunctional polyethyleneoxide-amines, monofunctional polyethyleneoxide-alcohols, polydimethylsiloxane-amines, and dodecylamines.

Polyurethane Preparation

The synthetic pathways will be generally discussed by reference to the particular examples provided. However, an artisan would know how to extend the knowledge acquired herein to the synthesis of other copolymers in accordance with this invention. The prepolymer, for example, may be made using a combination of different polyols or polyamines or mixtures thereof.

By means of example, in a two-stage reaction, MDI, PTMO, and dibutylamine may be first reacted to form an isocyanate-terminated prepolymer. Preferred conditions for this step are as follows. The prepolymer may then be chain extended with ethylene diamine (ED) at low temperatures, such as about 0° to 70° C., and preferably about 5° to 10° C.

to give a high molecular weight, segmented polymer. In a typical solution polymerization, e.g., using urethane-grade reactants and reagent grade solvents, enough water may be present as an impurity to consume a significant portion of the isocyanate groups present. This reaction will generate carbon dioxide and a urea group, that will couple two MDI residues with no methylene groups there between. These structures will be present in proportion to the amount of water present in the reactants and solvent. The hard segments produced in each reaction may be expected to contribute differently to the properties of the polymer, e.g., by changing the degree of phase separation from the soft segment. Many other reactions, such as side reactions, further complicate the structure of the polymer of the invention, thus making any simple-representation of the copolymer approximate. The side reactions may create difficulties for any prediction of structure vs. property relationships as well as increase the likelihood of batch-to-batch variations in the characteristics of the copolymer of the invention. The use of pure, dry reactants and anhydrous reaction conditions, and the use of chain-terminating reagents aids in the control of the overall polymer molecular weight minimizes side reactions and gives polymer structures more closely approximating the ideal or theoretical structure.

The diisocyanate and all reactants which contribute an active hydrogen, i.e., polyols, diamine, amines, may be added in a proportion of about 0.9 to 1.2 and more preferably about 0.95 to 1.1. The reactants may be added to a solvent of the following characteristics.

Suitable solvents are organic solvents that partially or completely stabilize or suspend the various reagents utilized in the preparation of the polymer. Preferred solvents are generally polar liquids and may include, but are not limited to, dimethylacetamide, dimethylformamide, dimethylsulfoxide, 2-methyoxyethanol, N-methoxyethanol, pyridine, and tetrahydrofuran. Combinations of these solvents may also be used. The solution of diisocyanate and polyalkylene oxide in a solvent is preferably about 40 to 85 wt % solids, more preferably about 50 to 80 wt % solids, and still more preferably about 75 wt % solids. However, it may be varied within a broader range.

The reagents and solvents should preferably be of high purity if the best results are desired. However, other grade reagents and solvents may also be utilized.

In general, as indicated above, the synthesis of polyurethanes is affected by moisture. Accordingly, all equipment utilized for synthesizing the copolymers of the invention should be thoroughly dried before use. All steps of the preparation thus should, in general, be maintained substantially water-free. Caution, in addition, should be exercised not to expose any reactants or solvents to atmospheric moisture. Moreover, some of the substances utilized for the synthesis of the copolymers of the invention, such as diphenylmethanediisocyanate (MDI), are highly toxic. Accordingly, the use of a respirator and gloves and adequate mechanical ventilation is recommended when handling them. Combustible solvents, such as dimethylformamide, which are suitable for use herein, are absorbed through the skin. Accordingly, any vapor breathing and skin contact with these compounds must be avoided.

The reaction may be conducted at a temperature of about 50° to 130° C., and more preferably about 55° to 60° C. for aromatic isocyanates and about 100° to 110° C. for aliphatic isocyanates, and a pressure of about 0.1 to 100 atm, and more preferably about 0.1 to 10 atm. Preferred are atmospheric pressure and an atmosphere free of moisture and oxygen. The reaction will in general go to completion in about 3 hours, and it may be conducted with agitation.

Of particular importance are the temperature ranges and the ratio or proportion of the reactants in the different reaction steps. The optimal reaction temperature for the reaction of aromatic diisocyanates with polyols is about 50° to 60° C. The optimal reaction temperature for the reaction of aliphatic diisocyanates with polyols is about 100° to 110° C. The optimal reaction temperature for amine terminated reactants is about 0° to 25° C. This reaction temperature applies to amines used as chain extenders and amines used in the soft segment. The diisocyanate and all reactants which contribute an active hydrogen, i.e., polyols, diamines, amines, may be added in a proportion of about 0.9 to 1.2 and more preferably about 0.95 to 1.1. The reactants may be added to a solvent as described above.

Although the copolymer of the invention may be prepared in a wide range of molecular weights, for some applications preferred is a molecular weight of about 5,000 to 1,000,000, and more preferable about 6,000 to 60,000. Still another range of preferred copolymer molecular weight is about 2,000 to 10,000, and more preferable about 3,000 to 6,000. Some of these may be used as prepolymers capable of further reaction during fabrication, whereas higher molecular weight homologues are utilized as the final polymers for preparation of the films such as membranes, sheets or hollow fibers.

Properties and Use: Fabrication of Formed Articles

Unconfigured SME-containing polymers may be converted to formed article by any method used to process the unmodified base polymers. These include melt processing methods such as extrusion, injection molding, compression molding, calendaring, and intensive mixing. SME polymers may also be processed by solution-based techniques such as spraying, dipping, casting, and coating. Water-based SME polymer emulsions can be fabricated by methods similar to those used for solvent based materials. In both cases the evaporation of a volatile liquid (e.g. organic solvent or water) leaves behind a film of the SME polymer. Crosslinking of the deposited film may be performed through the use of multi-functional reactive ingredients by a number of methods well known to those skilled in the art. For 100% solids, liquid SME polymer chain extension with optional crosslinking occurs during or after forming the configured article. The liquid system may cure by heat, moisture, high energy radiation, ultraviolet light, or by completing the reaction which produces the final polymer in a mold or on a substrate to be coated.

In general, surface-modifying endgroup can be expected to have little or no negative effect on processability. In fact, certain endgroups can enhance processability by favorably affecting wetting and spreading of the base polymer on mandrels or substrates to be coated. Other surface-related properties affected by SMEs may improve processability by improving mold release properties, mold filling surface smoothness of extrusions, polymer flow during compression molding, out-gassing and surface finish during solvent casting, coalescence of water-based emulsions, adhesion to substrates, antiblocking/self adhesion of films and profiles, and a variety other surface and bulk properties.

A polymer made from this composition will have the following characteristics: a tensile strength of from about 350 to about 10,000 psi, elongation at break from about 300 to about 1500%, an unsupported thickness of from about 5 to about 100 microns, and a supported thickness of from about 1 to about 100 microns.

Polymers according to the present invention can be used to make articles such as cardiac-assist devices, e.g. artificial hearts and intro-aortic balloons; catheters and catheter-introducers; pacemaker leads; vascular grafts; prosthetic implants, such as heart valves, ligaments, tendons, and joint replacements; condoms and condom coatings; and gloves and glove coatings.

This invention also provides a non-porous, semi-permeable, biocompatible film that comprises the block copolymer of the invention. In a preferred embodiment, the film is formed from the copolymer of this invention. In another preferred embodiment the film is coated onto a support. In still another preferred embodiment, the film is an integrated part of the substrate and is made of the same or similar polymer.

In particularly preferred embodiments, the non-porous film of the invention is provided in the form of a flexible sheet and a hollow membrane or fiber. Typically, the flexible sheet may be prepared as a long rollable sheet of about 10 to 15 inches width and 1 to 6 feet length. However, other dimensions may also be selected. Of particular importance is the thickness of the sheet which may be about 5 to 100 microns, and more preferably about 19 to 25 microns when it is to be used without support or reinforcement.

The flexible sheet is prepared from the block copolymer of the invention by methods known in the art, typically, by casting, and more preferably by casting on a web or release liner. As already indicated, the composition may be coated as a film onto a substrate. Where permanently supported on a reinforcing web, e.g., a fabric, the film or membrane may be thinner, e.g., as thin as about 1 micron, whereas when used unsupported the thickness may only be as low as about 5 to 10 microns.

When membranes are fabricated from the polymer of the invention by knife-over-roll casting onto a release paper, web, or liner in the form of dry films, they may have an about 1 to 100 micron nominal thicknesses on a continuous coating line. A 20-foot-long continuous web coater may be utilized having, e.g., a maximum web width of 15 inches equipped with two forced-air ovens. In one particular embodiment, the coater may be modified for clean operation by fitting the air inlet ducts with High Efficiency Particulate Air (HEPA) filters. A nitrogen-purged coater box may be used to hold and dispense filtered polymer solutions or reactive prepolymer liquids. However, other set-ups are also suitable.

All but trace amounts of a casting solvent, e.g., dimethylformide may be removed by coater's hot air ovens fitted with HEPA filters. After membrane casting, membrane and substrate may be further dried to reduce residual solvent content to less than about 100 ppm, as determined by liquid chromatography. The thickness of the fully-dried cast films may be measured by, e.g., using a spring micrometer sensitive to 0.0001 inch (2.5 AM) or visually by using a microscope.

The membrane of this invention may have any shape resulting from a process utilizing a liquid which is subsequently converted to a solid during or after fabrication, e.g., solutions, dispersions, 100% solids prepolymer liquids, polymer melts, etc. Converted shapes may also be further modified using methods such as die cutting, heat sealing, solvent or adhesive bonding or any of a variety of other commonly-used fabrication methods. For example, when in the form of a hollow tube, the membrane is generally prepared with a diameter of about 0.5 to 10 mm, and more preferably about 1 to 3 mm, and a thickness of about 1 to 100 microns, and more preferably about 19 to 25 microns. The hollow membrane may easily be prepared in long rollable form, and be cut to a length of about 0.75 to 31 inches, and more preferably about 0.5 to 6 inches.

Hollow fibers may be fabricated from the polymer solutions by dipping clean, dry, mandrels, e.g., a 1 mm diameter stainless steel mandrel into the polymer solution. The mandrel may be suspended in a baffled chamber maintained at above normal room temperature, e.g., about 27° to 50° C., in a Class 1,000 Cleanroom. The mandrel may be attached to a motor driven cable and dipped into the polymer solution and withdrawn at an even speed and the solvent may be allowed to evaporate. The mandrel may then be inverted, hung and dipped again. This procedure may be repeated, e.g., three times, to yield a tube with a single wall thickness of, e.g., 19 microns. Multiple dippings may be performed to reduce the chances of pinholes occurring in the polymer hollow fibers. The mandrels may then be left in the heated chamber for at least 16 hours to allow the solvent to evaporate. To aid in the removal of the hollow fibers from the mandrel, the coated mandrel may be soaked in distilled water for, e.g., one hour. The removal of any remaining residual solvent may be achieved by water extracting the hollow fibers in distilled water for, e.g., 24 hours. The hollow fibers may then be flushed three times with distilled water and packaged in distilled water in clean glass tubes. Prior to filling the hollow fibers they may be leak-tested. One end of the hollow fiber may be heat-sealed, the fiber filled with distilled water and the remaining end heat-sealed. The filled hollow fiber may then be pressurized and the tube examined for water leakage under pressure.

The fabrication methods just described employ liquid solutions or reactive liquid prepolymers of the membrane polymers. In the case of linear polymers of the present invention, thermoplastic fabrication methods may also be employed. Membrane polymers made by the bulk or solvent-free polymerization method described above may be cast into, e.g., a teflon-lined pan during the polymerization reaction. As the reaction proceeds and the polymerizing liquid becomes a rubbery solid, the pan may be postcured in an oven at, e.g., 100°–120° C. for about 1 hour. Upon cooling, the rubbery mass may be chopped into pellets and dried in a dehumidifying hopper dryer for, e.g., about 16 hours. The dry pellets may then be compression molded, e.g., at about 175° C. to form a flat membrane which, when cool, will leave a thickness of about 50 mm. Extrusion, injection molding, calendaring and other conversion methods that are well-known in the art may also be used to form membranes, films and coatings of the polymers of the present invention, including solid fibers, tubing, medical devices and prostheses, and all manner of configured articles, including toys.

EXAMPLES

Although the exemplary syntheses presented hereinbelow are based on polyurethane chemistry, it is within the scope of the present invention to append surface modifying endgroups to other segmented and block copolymers, random copolymers, graft copolymers and homopolymer. Of particular utility as base polymers in the present invention are block or segmented copolymers whose bulk properties are suitable for use in a particular application but whose surface properties are deficient in some way. The structure resulting from appending surface-modifying endgroups to a base polymer will vary with the starting structure of the base polymer. For example a base polymer with an original structure of

where B is one homopolymer block or segment (e.g. polyurea) and C is a different homopolymer block or segment (e.g. aliphatic polycarbonate) will have the following structure when appended to surface modifying endgroups A (e.g. polydimethylsiloxane):

Similarly if two different endgroups are used (e.g. A=polydimethylsiloxane and Z=polyethyleneoxide) the idealized structure would be represented as

Some particularly useful base polymer structures have C blocks of polyether, aliphatic polyester, polyisoprene, polyisobutylene, polybutadiene, polyethylenebutylene, and/or aliphatic polycarbonate and B blocks of polyurethane, polyurea, polyamide, aromatic polyester, aromatic polycarbonate, polystyrene, and/or polyacrylate.

In all of the above cases the subscript denotes that the alternating B and C blocks or segments repeat n times in the base polymer. Varying n changes the molecular weight of the base polymer. In this typical example the use of SMEs have essentially no effect on the original base polymer structure except at the free ends of the polymer chain. This is due to the use of monofunctional oligomers to produce the desired endgroup. Because of their single reactive group they can only occupy terminal positions in the base polymer. In contract the normally difunctional or multifunctional monomers or oligomers used to build the base polymer (e.g. B and C in the structures above) can continue to grow in two or more directions during synthesis leading to high molecular weight. Although it is within the scope of the present invention to incorporate branching and even crosslinking in the base polymer, the SMEs will reside only at the ends of linear chains or branches due to their nonfunctionality.

It is within the scope of the invention for the base polymer to have different structures than the alternating $[BC]_n$ shown above. In addition to the $[BC]_n$ structure the base polymer may have a homopolymer structure $[F]_n$ or a simpler copolymer structure such as BC or BCB or BCD, etc. where each letter denotes a different block or segment. In each case the structure of the surface modified version includes the original base polymer as the central structure and one or more surface modifying moieties appended to each terminus of the base polymer. For example the above structures with a single endgroup chemistry represented by "A" would have the following structures when appended with the surface modifying endgroup: $A[F]_nA$, ABCA, ABCBA, ABCDA, etc. If two different endgroups are employed one denoted as A and the other denoted as "Z" the above structures become $A[F]_nZ$, ABCZ, ABCBZ, ABCDZ, etc. Thus the possible variety of structures of surface modified polymers is actually greater than the variety of structures possible with the base polymer alone, since the endgroups constitute additional structural variables.

At first consideration it may appear that a linear polymer may have only two chemically-different surface-modifying endgroups (one for each end of the linear chain), this is not so. During synthesis it is possible to use a mixture consisting of more than two different monofunctional oligomeric endgroups. When this is done, no single chain can have more than two chemically-different endgroups. However the population of individual chains that comprise the polymeric product of the synthesis can have a variety of endgroups in combinations of two as determined by the initial reactor charge. Thus it is possible to synthesize a surface-modified polymer product which consists of a distribution of polymers, all of which have similar mid blocks (the base polymer) but which have different combinations of end blocks. This may be useful for producing surfaces which can minimize interfacial energy in a wide variety of environments by 'delivering' the best surface-modifying endgroup to the polymer surface, depending on the nature of the interface encountered. The use of multiple (>1) endgroup chemistries may also be used for simultaneously providing more than one functionality to the surface. One example of the latter approach is the use of hydrophobic, e.g polydialkylsiloxane (MPSX), and hydrophilic endgroups e.g. polyethyleneoxide (MPEO), in a blood-contacting surface to improve blood compatibility. The same polymer might also incorporate a sulphonated chain as a third endgroup to provide active anticoagulation properties to the surface, for example. In this case some polymer chains will have two MPSX endgroups, other chains will have two MPEO endgroups or two sulphonated endgroups. Still other polymer chains will have combinations comprising any two of the three different end-groups. In branched or crosslinked SME polymers a single polymer molecule may have as many different endgroups as it has terminal ends. Of course, the possible combinations of different endgroups on a single polymer molecule increases dramatically as the number of termini per molecule increases, due to branching or crosslinking.

The copolymers of the invention may be prepared by one-step, two-step, or three-step synthetic methods depending on the complexity of the chemical structure desired. Examples of polymers prepared by all three methods are provided below.

Example 1—One-Step Synthesis

In the one-step synthesis, all the reactants are added to the reaction chamber at the same time. A polymer product according to the present invention that can be made by the one-step method is shown in the following structural formula:

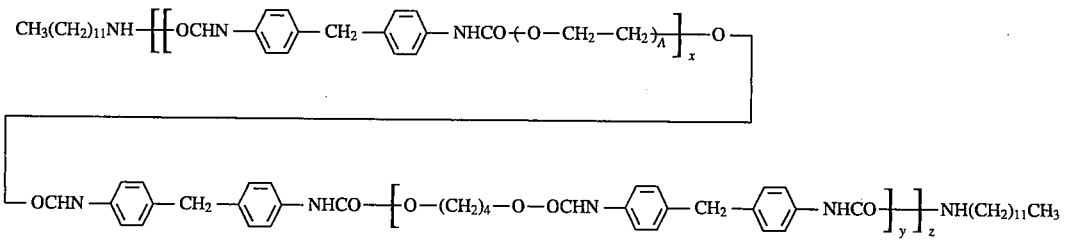

wherein
- A is about 4 to 23000, preferably about 4 to 180;
- x is about 1 to 25, preferably about 1 to 15;
- y is about 1 to 20, preferably about 1 to 10; and
- z is about 1 to 20, preferably about 1 to 10.

Example 2—Two-Step Synthesis

A polymer product according to the present invention that can be made by the two-step method is shown in the following structural formula:

Example 3—Three Step Synthesis

A polymer product according to the present invention that can be made by the three-step method is shown in the following structural formula:

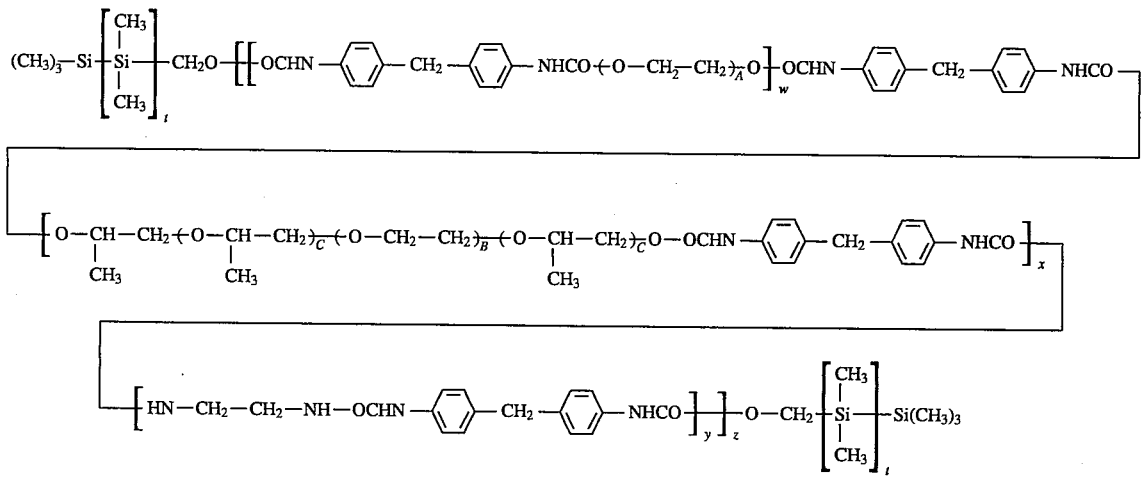

wherein
A is about 1 to 23000, preferably about 4 to 180;

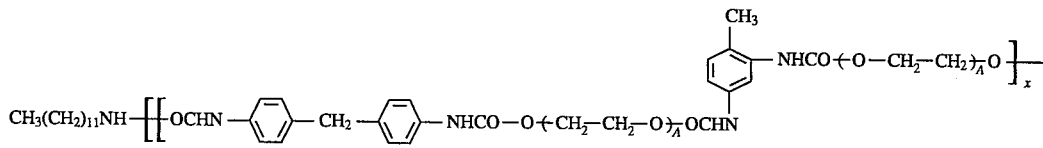

- B is about 4 to 400, preferably about 4 to 200;
- C is about 1 to 100, preferably about 4 to 75;
- w is about 1 to 25, preferably about 1 to 15;
- x is about 1 to 25, preferably about 1 to 15;
- y is about 1 to 20, preferably about 1 to 10; and
- z is about 1 to 20, preferably about 1 to 10.

wherein
- A is about 4 to 23000, preferably about 4 to 180;
- x is about 1 to 25 preferably about 4 to 15;

y is about 1 to 25, preferably about 4 to 15; and z is about 1 to 20, preferably about 4 to 10.

Exemplary Syntheses

Those skilled in the art can prepare any of the polymers described in Examples 1 through 9 hereinbelow as a solution-based polymer (dissolved in an organic solvent), as a thermoplastic polymer (100% solids, no solvent), as a waterborne emulsion or dispersion (polymer dispersed in a water phase), or as a two-component castable polymer. Synthesis procedures are described below which would enable the preparation of a multitude of polymers by changing soft segments, isocyanates, chain extenders and/or endgroups. It will be understood by those skilled in the art that reactants identified below simply as polymers, e.g. polytetramethylene oxide, actually contain reactive groups, e.g. terminal hydroxy groups.

Solution-based Synthesis

Soft Segment: Polytetramethylene oxide (PTMO)

Hard Segment: 4,4'-diphenylmethane diisocyanate (MDI), ethylene diamine (ED) and 1,3 cyclohexanediamine (CHD)

Endgroup: dodecylamine (DDA)

| Reactant | Molecular Weight | %, by weight | moles |
| --- | --- | --- | --- |
| PTMO | 1906 | 77.98 | 6.685 |
| MDI | 250.26 | 18.71 | 12.22 |
| ED | 60.1 | 1.49 | 4.08 |
| CHD | 114.19 | 0.69 | 0.99 |
| DDA | 185.36 | 1.13 | 1 |

Charge reactor with 779.8 grams (0.4091 moles) of polytetramethylene oxide (PTMO) and 11.3 grams (0.0610 moles) of dodecylamine (DDA) and dry under vacuum with a nitrogen purge.

Add 4,4'-diphenylmethane diisocyanate (MDI) solution (187.1 grams MDI (0.7476 moles) and 561.3 grams of dimethylacetamide (DMAC)).

Dilute the contents of the reactor with 860 grams of DMAC.

Stir ingredients for 3 hours at 55°±2° C.

Dilute the contents of the reactor with 860 grams of DMAC.

Cool the reactor contents to 40°±2° C.

Complete the polymer synthesis by adding 14.9 grams (0.2479 moles) of ethylene diamine (ED), and 6.9 grams (0.0604 moles) of 1,3 cyclohexane diamine (CHD) and 65 grams of DMAC.

Stir for 30 minutes at 40°±2° C.

Empty the reactor.

The structure of a typical polymer from a solution-based synthesis having MDI/ED/CHD hard segments, PTMO soft segments, and DDA endgroups is depicted in FIG. 1, wherein the portion of the structure that is within bold brackets is the base polymer and the surface active endgroups are identified. The variables n, w, x, y, and z denote degrees of polymerization of blocks and segments within the base polymer.

Figure 6:
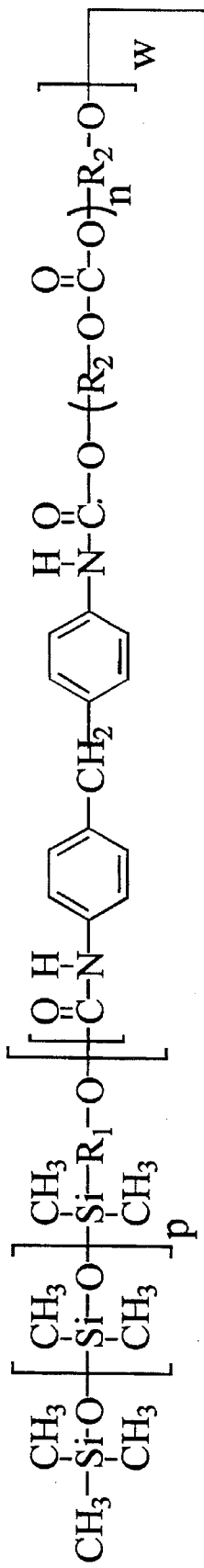
FIG. 6 depicts the structure of a typical polymer having polycarbonate soft segments prepared by means of solution-based synthesis according to the present invention.
Figure 6:
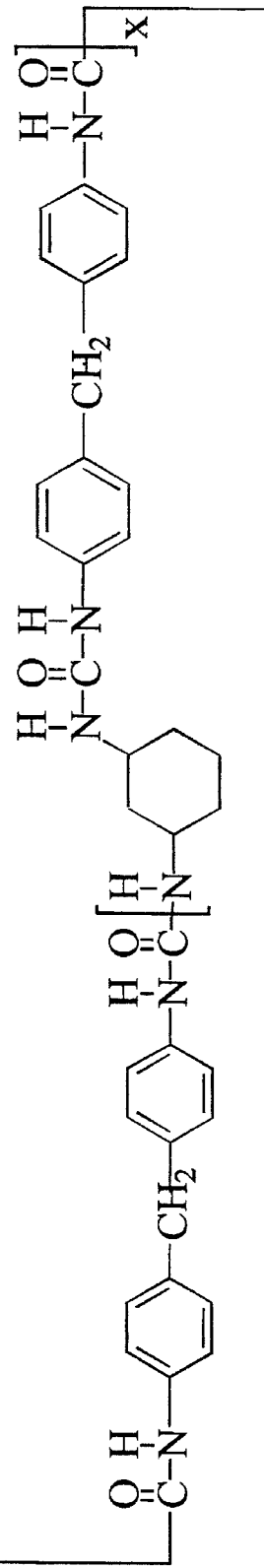
Figure 6:
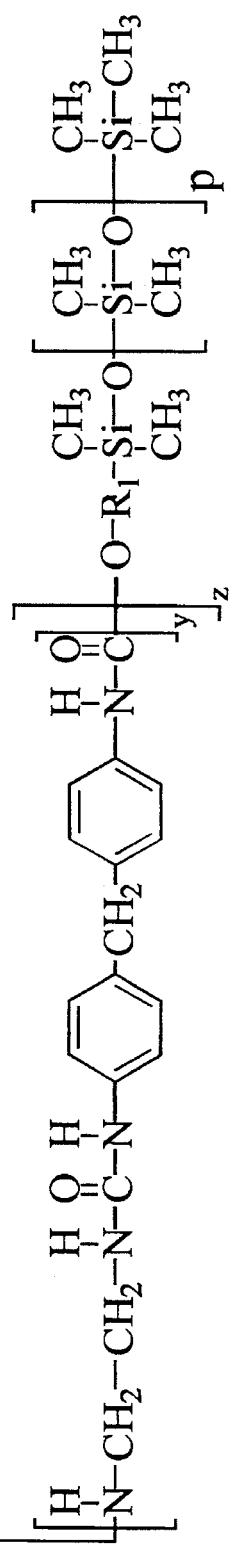
Figure 7:
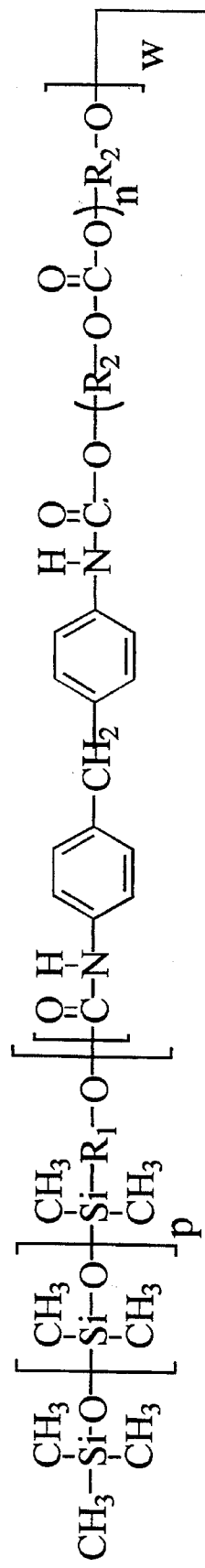
FIG. 7 depicts the structure of a typical polymer having polycarbonate soft segments prepared by means of solution-based synthesis according to the present invention.
Figure 7:
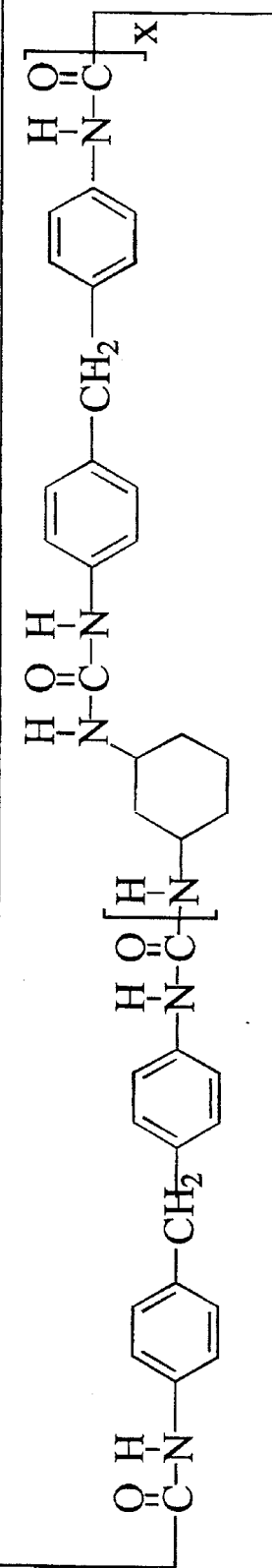
Figure 7:
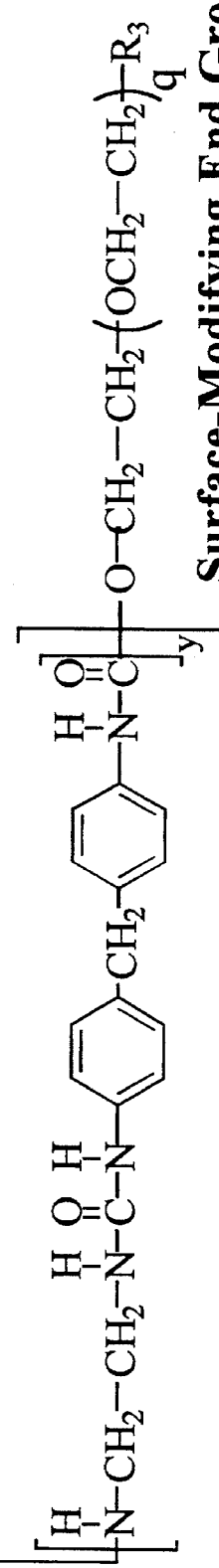
Figure 8:
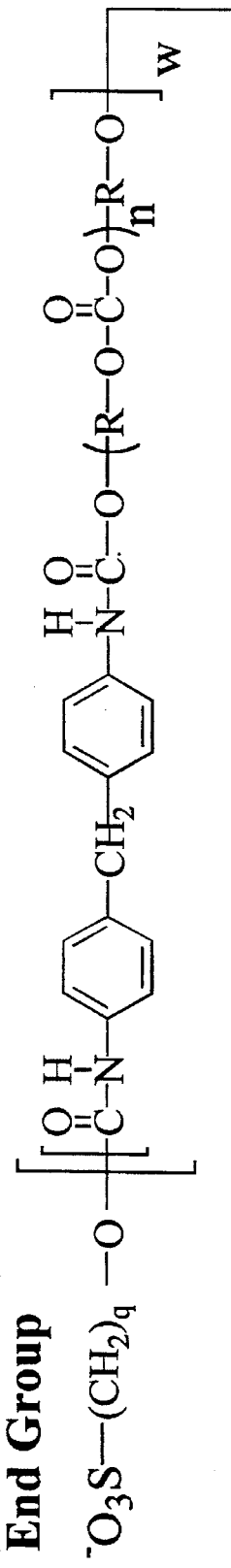
FIG. 8 depicts the structure of a typical polymer having polycarbonate soft segments prepared by means of solution-based synthesis according to the present invention.
Figure 8:
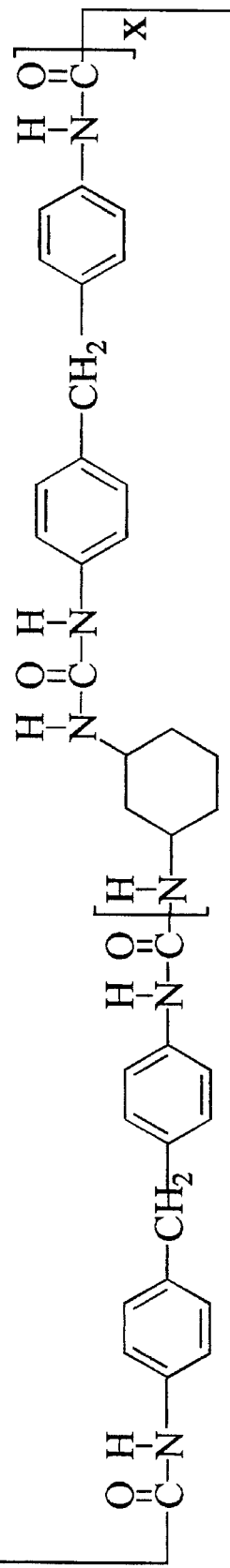
Figure 8:
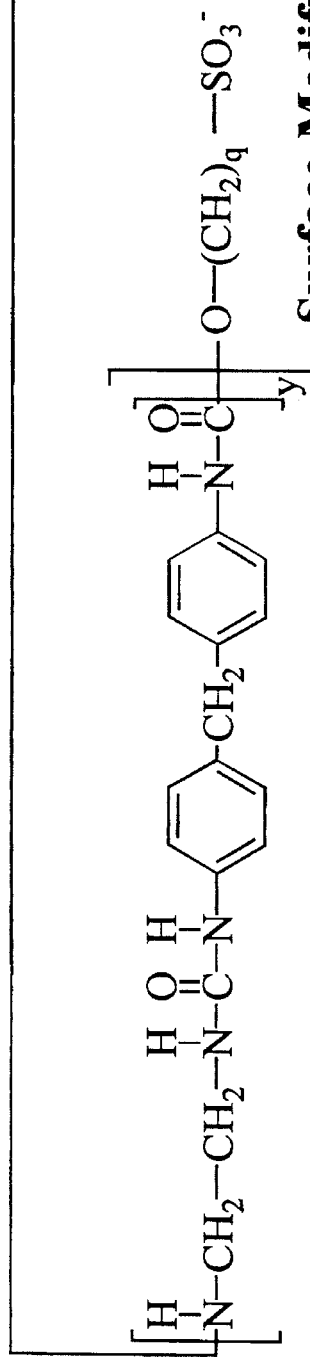

Other typical polymer structures prepared by solution-based syntheses are shown in FIG. 6, FIG. 7, and FIG. 8, wherein $R_1$ is alkyl or aryl, $R_2$ is alkyl containing 4 to about 10 carbons or cycloaliphatic, n is 4 to about 50, $R_3$ is a non-reactive group such as n-alkyl, methyl-terminated alkyleneoxide, and the like, and p and q is each independently greater than 2. In each of these cases as in the case depicted in FIG. 1, the hard segments are MDI/ED/CHD. In all of these cases, it should be noted that the use of the mixed ethylenediamine (ED)/1,3-cyclohexanediamine (CHD) chain extender is optional, and that one or more chain-extending diols or diamines may be used instead. The soft segments shown in FIG. 6, FIG. 7, and FIG. 8 are polycarbonates. Although the endgroups shown in FIG. 6, FIG. 7, and FIG. 8 are polydimethylsiloxanes, other suitable surface-modifying endgroups which may be used alone or in combination with one another include hydrocarbons, fluorocarbons, fluorinated polyethers, polyalkylene oxides, various sulphonated groups, and the like.

Water-borne Synthesis

Soft Segment: Polytetramethylene oxide (PTMO) and Polypropylene oxide-polyethylene oxide copolymer (PPO-MPEO)

Hard Segment: dicyclohexylmethane 4,4'-diisocyanate (HMDI), ethylene diamine (ED) and 2,2'-bis(hydroxy methyl) propionic acid (DMPA)

Endgroup: monofunctional OH-terminated polydimethylsiloxane (MPSX)

Base: triethylamine (TEA), neutralizes acid groups on DMPA

| Reactant | Molecular Weight | %, by weight | moles |
| --- | --- | --- | --- |
| PTMO | 1000 | 20.79 | 8.66 |
| PPO-PEO | 1972 | 38.53 | 8.14 |
| HMDI | 262 | 29.94 | 47.6 |
| ED | 60.1 | 3.13 | 21.7 |
| DMPA | 134.13 | 2.79 | 8.66 |
| MPSX | 2000 | 4.82 | 1 |
| TEA | 101.19 | 2.10 | 8.66 |

Melt and dry under vacuum 332.64 grams (0.33264 moles) of polytetramethylene oxide (PTMO) and 616.48 grams (0.03126 moles) of polypropylene oxide-polyethylene oxide copolymer (PPO-PEO). Add to the reactor.

Add 44.64 grams (0.3328 moles) of 2,2"-bis(hydroxy methyl) propionic acid (DMPA) and 77.12 grams (0.03856 moles) of monofunctional OH-terminated polydimethylsiloxane (MPSX).

Add 479.04 grams (1.8284 moles) of dicyclohexylmethane 4,4'-diisocyanate (HMDI).

Add 0.06 grams of Stannous Octoate.

Stir ingredients for 45 minutes at 100°±2° C.

Cool the reactor contents to 65°+2° C.

Add 33.68 grams (0.3328 moles) of triethylamine (TEA)

Stir for 15 minutes at 65°±2° C.

Prepare a solution of 21.7 grams (0.3611 moles) of ethylene diamine (ED) in 100 grams of distilled water.

Disperse prepolymer with 6400 grams of distilled water. Stir for 10 minutes.

Add the ED solution. Stir for one hour.

Remove solution from reactor and filter through a ASTM No. 50 sieve.

Figure 2:
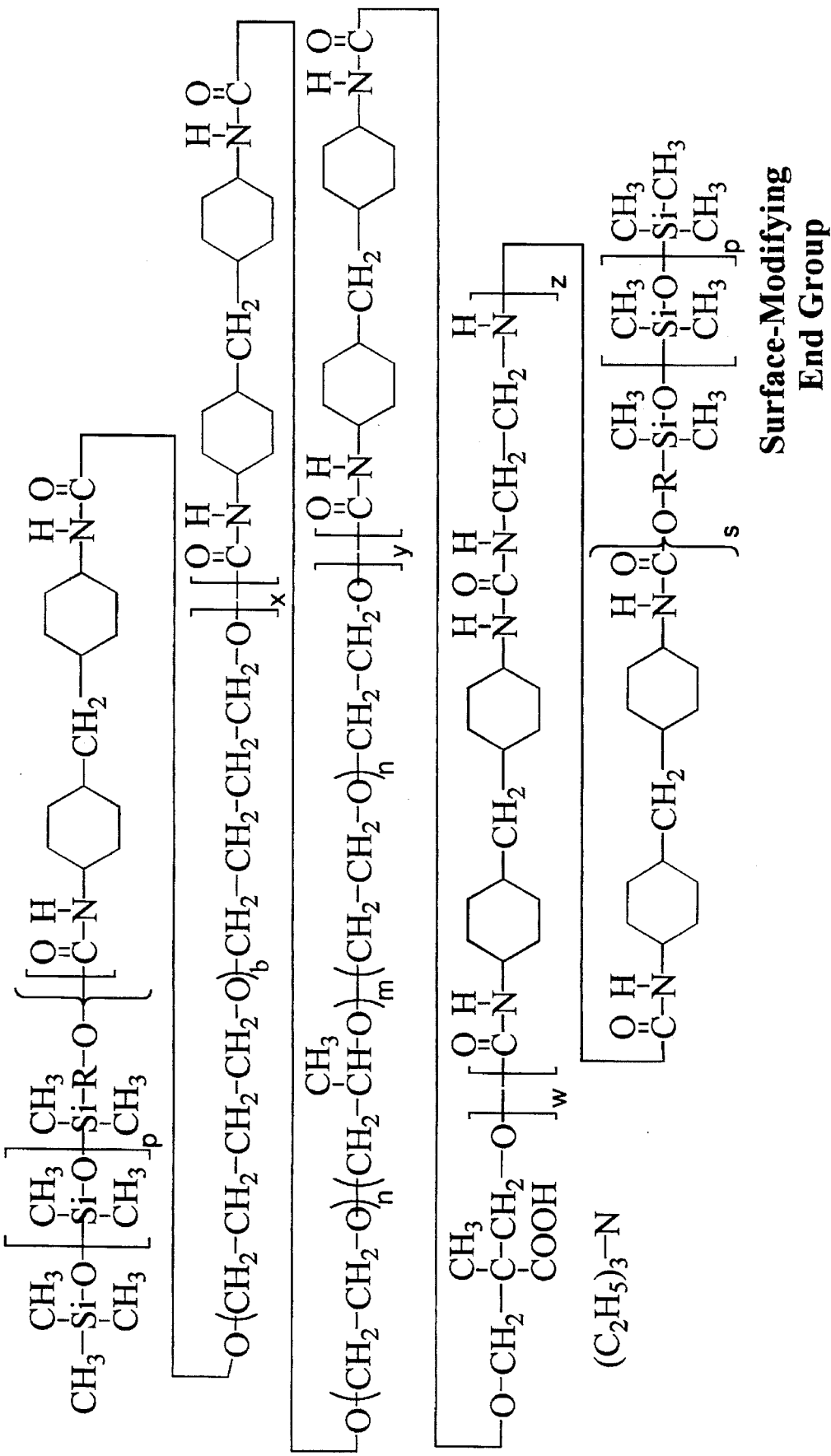
FIG. 2 depicts the structure of a typical polymer having PTMO and PPO-PEO copolymer soft segments prepared by means of water-borne (emulsion) synthesis according to the present invention.

The structure of a typical polymer from a water-borne synthesis having MDI/ED/DMPA hard segments, PTMO and PPO-PEO copolymer soft segments, and MPSX endgroups is depicted in FIG. 2, wherein the portion of the structure that is within bold brackets is the base polymer and the surface active endgroups, in which R is an alkylene linkage, are identified. The variables p, b, x, n, m, y, w, z, and s denote degrees of polymerization of blocks and segments within the base polymer and endgroups.

Bulk (Thermoplastic) Synthesis

Soft Segment: Polytetramethylene oxide (PTMO)

Hard Segment: 4,4'-diphenylmethane diisocyanate (MDI), and butanediol (BD)

Endgroup: monofunctional OH-terminated polydimethylsiloxane (MPSX)

| Reactant | Molecular Weight | %, by weight | moles |
|---|---|---|---|
| PTMO | 1906 | 65.19 | 11.71 |
| MDI | 250.26 | 23.56 | 32.23 |
| BD | 60.1 | 5.41 | 20.05 |
| MPSX | 2000 | 5.84 | 1 |

Change reactor with 651.9 grams (0.3420 moles) of polytetramethylene oxide (PTMO) and 58.4 grams (0.0292 moles) of monofunctional OH-terminated polydimethylsiloxane (MPSX) and dry under vacuum with a nitrogen purge.

Add 235.6 grams (0.9414 moles) 4,4'-diphenylmethane diisocyanate (MDI).

Stir ingredients for 30 minutes at 110°±5° C.

Complete the polymer synthesis by adding 54.1 grams (0.600 moles) of butanediol (BD).

Stir for one minute. Empty the reactor.

Figure 3:
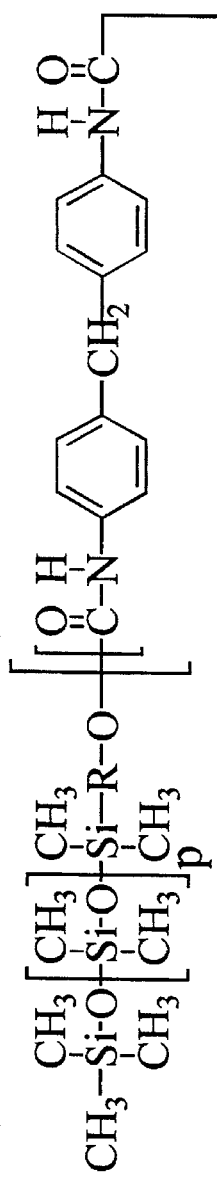
FIG. 3 depicts the structure of a typical thermoplastic polymer having PTMO soft segments prepared by means of bulk polymerization according to the present invention.
Figure 3:
Figure 3:
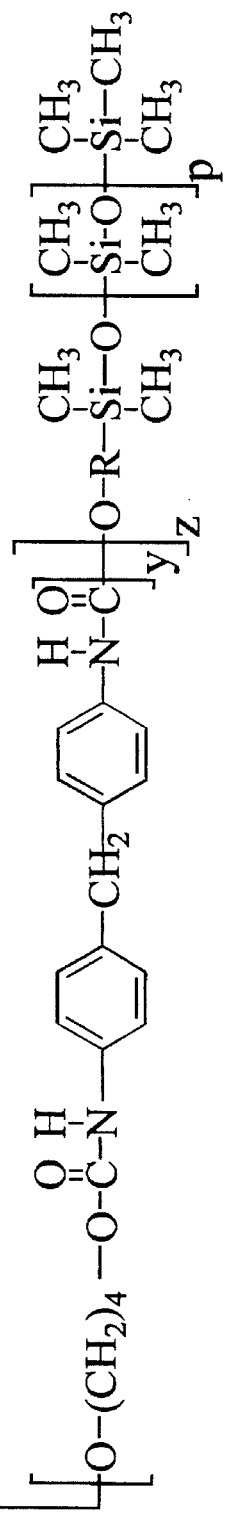

The structure of a typical polymer from a bulk synthesis having MDI/BD hard segments, PTMO soft segments, and MPSX endgroups is depicted in FIG. 3, wherein the portion of the structure that is within bold brackets is the base polymer and the surface active endgroups, in which R is an alkylene linkage, are identified. The variables p, n, x, y, and z denote degrees of polymerization of blocks and segments within the base polymer and endgroups.

Figure 5:
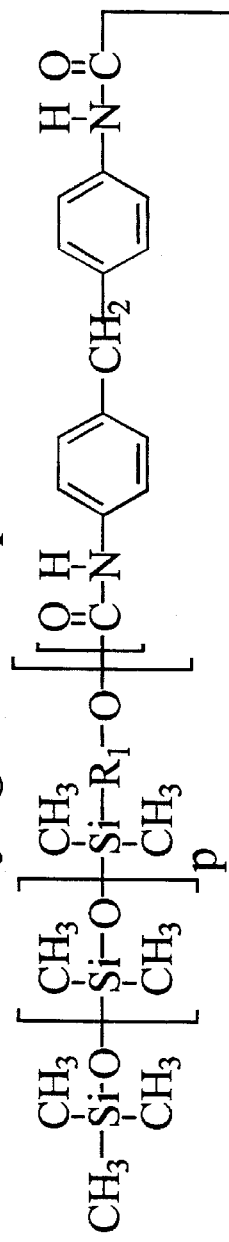
FIG. 5 depicts the structure of a typical polymer having polycarbonate soft segments prepared by means of bulk polymerization according to the present invention.
Figure 5:
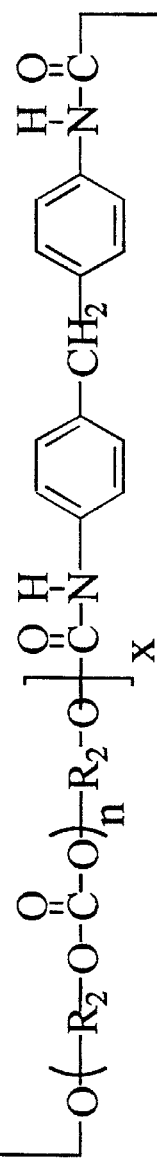
Figure 5:
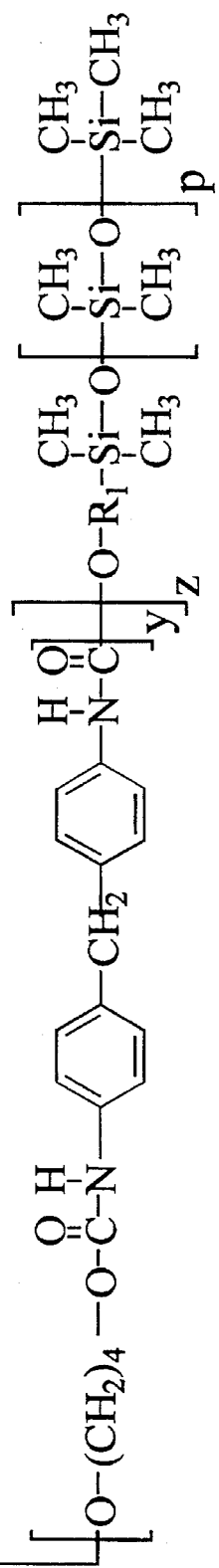

Other typical polymer structures prepared by bulk syntheses are shown in FIG. 5, wherein $R_1$ is alkyl or aryl, $R_2$ is alkyl containing 4 to about 10 carbons or cycloaliphatic, and n is 4 to about 50. In this case, it should be noted that the use of the butanediol (BD) chain extender is optional, and that one or moe chain-extending diols or diamines may be used instead. The soft segments shown are polycarbonates. Although the endgroups shown are polydimethylsiloxanes, other suitable surface-modifying endgroups which may be used alone or in combination with one another include hydrocarbons, fluorocarbons, fluorinated polyethers, polyalkylene oxides, various sulphonated groups, and the like.

Two-Component Castable Prepolymer Synthesis

Soft Segment: Polytetramethylene oxide (PTMO)

Hard Segment: 4,4'-diphenylmethane diisocyanate (MDI)

Endgroup: monofunctional OH-terminated polydimethylsiloxane (MPSX)

| Reactant | Molecular Weight | %, by weight | moles |
|---|---|---|---|
| PTMO | 1906 | 71.59 | 6.69 |
| MDI | 250.26 | 17.18 | 12.22 |
| MPSX | 2000 | 11.23 | 1 |

Change reactor with 171.8 grams (0.6865 moles) of 4,4'-diphenylmethane diisocyanate (MDI) at 60° C.

Add 715.9 grams (0.3756 moles) of polytetramethylene oxide (PTMO) and 112.4 grams (0.0562 moles) of monofunctional OH-terminated polydimethylsiloxane slowly to keep the exotherm between 60° and 90° C.

The reaction is conducted for 3 hours.

This will result in a prepolymer partially terminated with MPSX and containing an excess of isocyanate (NCO). The polymer is cross-linked using 25.30 grams (0.1885 moles) trimethylolpropane.

Alternatively, blends of diols and triols may be used for the cross-linking step provided that approximately stoichiometric amounts of —OH equivalents (based on free —NCO of the prepolymer) are employed.

Figure 4:
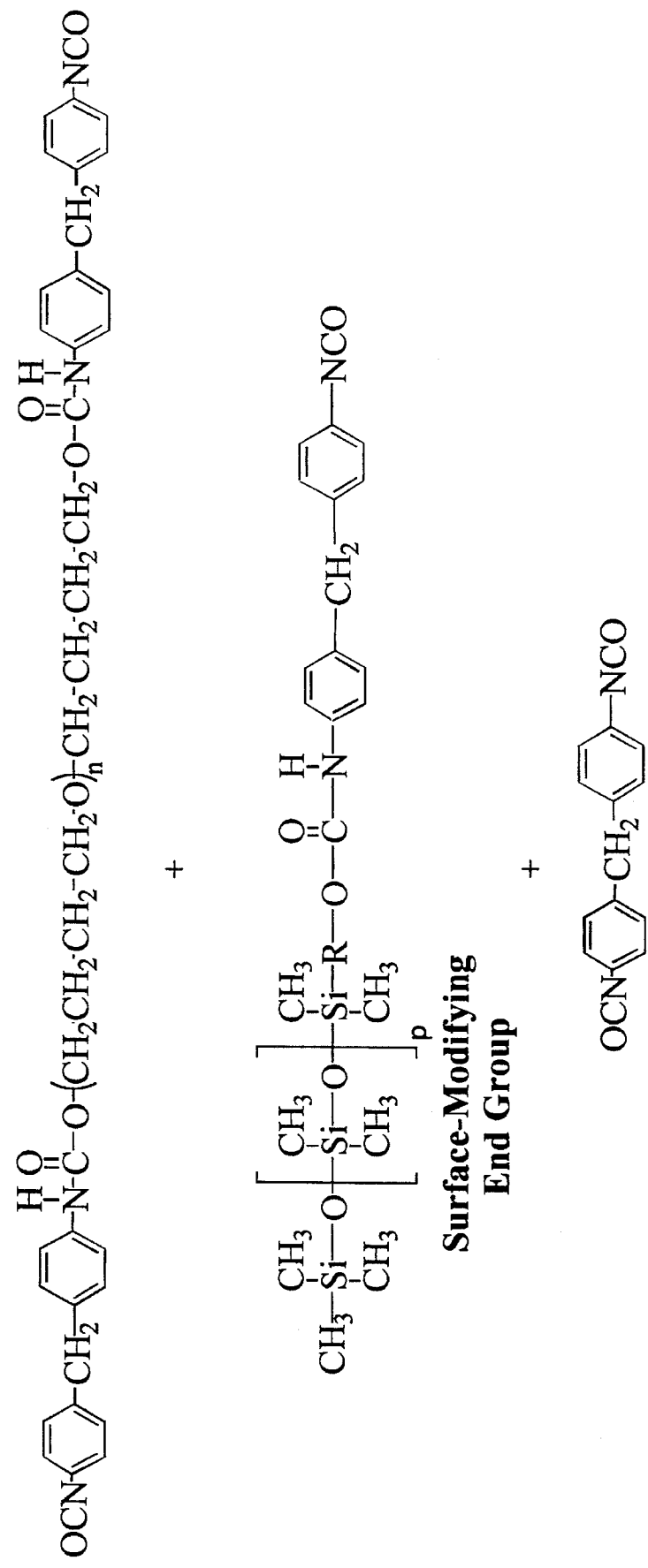
FIG. 4 depicts the structure of a typical polymer having PTMO soft segments prepared by means of two-component castable liquid prepolymer synthesis according to the present invention.

The structure of a typical reactants that may be used to form a polymer according to the two-component castable prepolymer synthesis of the present invention having MDI hard segments, PTMO soft segments, and MPSX endgroups is depicted in FIG. 4, wherein the surface active endgroups, in which R is an alkylene linkage, are identified in the reaction product of MPSX with MDI, which is used to introduce the MPSX into the final product. The variables n and p denote degrees of polymerization within the base polymer soft segments and endgroups. The final polymer may be formed from the components depicted by the addition of trimethylolpropane crosslinker. Alternatively, the components may be crosslinked by blends of diols and triols.

SYNTHESIS EXAMPLES

Example 1

A segmented polyurethane block copolymer is prepared by reacting the soft segment precursor polyol(s) and surface active endgroup precursor(s) with the hard segment polyisocyanate precursor(s) according to any one of the synthetic procedures described hereinabove. The endgroup used in this case, diethylamine, generally does not provide surface active properties as contemplated by the present invention. The reactant amounts are as follows:

| Reactant | Molecular Weight | %, by weight | moles |
|---|---|---|---|
| PTMO | 1906 | 79.30 | 13.87 |
| MDI | 250.26 | 18.34 | 24.43 |
| ED | 60.1 | 1.46 | 8.10 |
| CHD | 114.19 | 0.68 | 1.98 |
| DEA | 73.14 | 0.22 | 1 |

Soft Segment: Polytetramethylene oxide (PTMO)

Hard Segment: 4,4'-diphenylmethane diisocyanate (MDI), ethylene diamine (ED) and 1,3 cyclohexanediamine (CHD)

Endgroup: diethylamine (DEA)

Example 2

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PTMO | 1906 | 75.01 | 12.69 |
| MDI | 250.26 | 16.89 | 21.77 |
| ED | 60.1 | 1.28 | 6.87 |
| CHD | 114.19 | 0.61 | 1.73 |
| MPSX | 2000 | 6.21 | 1 |

Soft Segment: Polytetramethylene oxide (PTMO)

Hard Segment: 4,4'-diphenylmethane diisocyanate (MDI), ethylene diamine (ED) and 1,3 cyclohexanediamine (CHD)

Endgroup: monofunctional OH-terminated polydimethylsiloxane (MPSX)

Example 3

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PC | 1723 | 76.19 | 6.67 |
| MDI | 250.26 | 20.22 | 12.17 |
| ED | 60.1 | 1.61 | 4.03 |
| CHD | 114.19 | 0.75 | 1 |
| DDA | 185.36 | 1.23 | 1 |

Soft Segment: Polycarbonate polyol (PC)

Hard Segment: 4,4'-diphenylmethane diisocyanate (MDI), ethylene diamine (ED) and 1,3 cyclohexanediamine (CHD)

Endgroup: dodecylamine (DDA)

Example 4

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PC | 1723 | 73.03 | 13.87 |
| MDI | 250.26 | 18.68 | 24.43 |
| ED | 60.1 | 1.49 | 8.1 |
| CHD | 114.19 | 0.69 | 1.98 |
| MPSX | 2000 | 6.11 | 1 |

Soft Segment: Polycarbonate polyol (PC)

Hard Segment: 4,4'-diphenylmethane diisocyanate (MDI), ethylene diamine (ED) and 1,3 cyclohexanediamine (CHD)

Endgroup: monofunctional OH-terminated polydimethylsiloxane (MPSX)

Example 5

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PTMO | 1906 | 75.77 | 6.71 |
| MDI | 250.26 | 20.11 | 12.27 |
| ED | 60.1 | 1.60 | 4.08 |
| CHD | 114.19 | 0.74 | 1 |
| FA | 443 | 1.78 | 1 |

Soft segment: Polytetramethylene oxide (PTMO)

Hard Segment: 4,4'-diphenylmethane diisocyanate (MDI), ethylene diamine (ED) and 1,3 cyclohexanediamine (CHD)

Endgroup: fluoroalkyl alcohol (FA)

Example 6

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PPO-PEO | 1972 | 7.98 | 2 |
| PEO | 1475 | 53.0 | 7.98 |
| MDI | 250.26 | 19.94 | 18.98 |
| ED | 60.1 | 2.16 | 7.98 |
| MPSX | 2000 | 8.94 | 1 |
| MPEO | 2000 | 7.98 | 1 |

Soft Segment: Polyethylene oxide (PEO) and Polypropylene oxide-polyethylene oxide copolymer (PPO-PEO)

Hard Segment: 4,4'-diphenylmethane diisocyanate (MDI), ethylene diamine (ED) and 1,3 cyclohexanediamine (CHD)

Endgroup: monofunctional OH-terminated polydimethylsiloxane (MPSX) and monofunctional amine terminated polyethylene oxide (MPEO)

Example 7

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PIB | 2000 | 75.86 | 13.87 |
| MDI | 250.26 | 16.72 | 24.43 |
| ED | 60.1 | 1.33 | 8.10 |
| CHD | 114.19 | 0.62 | 1.98 |
| MPSX | 2000 | 5.47 | 1 |

Soft Segment: Polyisobutylene (PIB)

Hard Segment: 4,4'-diphenylmethane diisocyanate (MDI), ethylene diamine (ED) and 1,3 cyclohexanediamine (CHD)

Endgroup: monofunctional OH-terminated polydimethylsiloxane (MPSX)

Example 8

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PIB | 2000 | 71.18 | 6.69 |
| MDI | 250.26 | 16.27 | 12.22 |
| ED | 60.1 | 1.30 | 4.05 |
| CHD | 114.19 | 0.60 | 1 |
| MPEO | 2000 | 10.65 | 1 |

Soft Segment: Polyisobutylene (PIB)

Hard Segment: 4,4'-diphenylmethane diisocyanate (MDI), ethylene diamine (ED) and 1,3 cyclohexanediamine (CHD)

Endgroup: monofunctional amine terminated polyethylene oxide (MPEO)

Example 9

A segmented polyurethane block copolymer according to the present invention is prepared by reacting the soft segment precursor polyol(s) and surface active endgroup precursor(s) with the hard segment polyisocyanate precursor(s) according to any one of the synthetic procedures described hereinabove. The reactant amounts are as follows:

| Reactant | Molecular Weight | %, by weight | moles |
|---|---|---|---|
| PBD | 2800 | 77.57 | 6.69 |
| MDI | 250.26 | 12.67 | 12.22 |
| ED | 60.1 | 1.01 | 4.05 |
| CHD | 114.19 | 0.47 | 1 |
| MPSX | 2000 | 8.28 | 1 |

Soft Segment: Polybutadiene polyol (PBD)

Hard Segment: 4,4'-diphenylmethane diisocyanate (MDI), ethylene diamine (ED) and 1,3 cyclohexanediamine (CHD)

Endgroup: monofunctional OH-terminated polydimethylsiloxane (MPSX)

The present invention has been illustrated by reference to certain specific embodiments thereof. However, those skilled in the art will readily appreciate that other, different embodiments can be practiced using the principles of the invention. All said embodiments constitute a part of the invention patented to the extent that they are reflected in the appended claims.

What is claimed is:

1. A surface active endgroup-containing polymer that comprises a linear base polymer having covalently bonded surface active endgroups of a nature and present in an amount such that said polymer has a surface or interfacial tension that differs by at least 1 dyne/cm from the surface or interfacial tension of an otherwise identical polymer having diethylamino endgroups.

2. The surface active endgroup-containing polymer according to claim 1 wherein said polymer has a surface or interfacial tension that differs by at least 5 dynes/cm from the surface or interfacial tension of an otherwise identical polymer having diethylamino endgroups.

3. The surface active endgroup-containing polymer according to claim 1 wherein said linear base polymer is a polyurethane to which said endgroups are linked through isocyanate linkages.

4. The surface active endgroup-containing polymer of claim 1, wherein said endgroup is selected from the group consisting of monofunctional aliphatic polyols, aliphatic or aromatic amines, and mixtures thereof.

5. The surface active endgroup-containing polymer of claim 4, wherein
   (a) the monofunctional aliphatic polyols of the endgroup are selected from the group consisting of monofunctional polyalkylene oxides, siloxanes, fluorinated alkanols, and mixtures thereof; and
   (b) the monofunctional amines of the endgroup are selected from the group consisting of alkylamines, dialkylamines, amine-functionalized siloxanes, amine-terminated polyalkylene oxides, fluorinated alkylamines, and mixtures thereof.

6. The surface active endgroup-containing polymer according to claim 1 wherein said block copolymer is a polyurethaneurea and said surface active endgroup is an alkyl or dialkylamine.

7. The surface active endgroup-containing polymer according to claim 1 wherein said block copolymer is a polyurethaneurea and said surface active endgroup is a polydimethylsiloxane-amine.

8. The surface active endgroup-containing polymer according to claim 1 wherein said block copolymer is a polyurethaneurea and said surface active endgroup is selected from the group consisting of monofunctional polyethyleneoxide-amines and monofunctional polyethyleneoxide-alcohols.

9. The surface active endgroup-containing polymer of claim 1, having a molecular weight of about 5,000 to 150,000.

10. The surface active endgroup-containing polymer of claim 1 having at least one hard and one soft segment, wherein the aliphatic polyols of the soft segment are selected from the group consisting of linear, branched, and graft polyarylene, polyalkylene, and polyalkenylene oxides, random and block copolymers thereof, polycarbonate polyols, hydroxyl-terminated silicones, random and block copolymers thereof with polyalkylene oxides, linear and branched polyalkenyl, and polyalkylene polyols, and mixtures thereof.

11. The surface active endgroup-containing polymer of claim 10, wherein the soft segment is selected from the group consisting of amine-terminated polyalkylene oxides and random, block and graft copolymers thereof, amine-terminated polydialkylsiloxanes, random and block copolymers thereof with polyalkylene oxides, and mixtures thereof.

12. The surface active endgroup-containing polymer of claim 1, wherein the soft segment is selected from the group consisting of reaction products of an organic diisocyanate with a polyamine and a polyol.

13. The surface active endgroup-containing polymer of claim 10, wherein the organic diisocyanate of the hard segment is selected from the group consisting of alkyl diisocyanates, arylalkyldiisocyanates, alkyl-cycloalkyl diisocyanates, alkylaryl diisocyanates, cycloalkyl diisocyanates, aryl diisocyanates, and cycloalkylaryl diisocyanates, which may be further substituted with oxygen, and mixtures thereof.

14. The surface active endgroup-containing polymer of claim 13, wherein the polyol of the hard segment is selected from the group consisting of alkylene, cycloalkylene and arylene diols, triols, tetraalcohols, pentaalcohols, and mixtures thereof.

15. The surface active endgroup-containing polymer of claim 13, wherein the polyamine of the hard segment is selected from the group consisting of alkyl, cycloalkyl, and aryl amines, which may be further substituted with N, O, or halogen, complexes thereof with alkali metal salts, and mixtures thereof.

16. The surface active endgroup-containing polymer of claim 10, wherein the soft segment comprises a polyethyleneoxide of molecular weight greater than about 3,000 daltons.

17. The surface active endgroup-containing polymer of claim 16, wherein the polyethyleneoxide has a molecular weight of about 8,000 daltons or greater.

18. The surface active endgroup-containing polymer of claim 17, wherein the soft segment comprises a blend of polyols selected from the group consisting of a polyethyleneoxide of molecular weight greater than about 3,000 daltons, a polyethyleneoxide-polytetramethyleneoxide copolymer and a polyethyleneoxide homopolymer, a polyethyleneoxide-polytetramethyleneoxide copolymer and an ethyleneoxide-capped polyethyleneoxide copolymer, a polyethyleneoxide-polypropyleneoxide copolymer and a polyethyleneoxide homopolymer, a polyethyleneoxide-polypropyleneoxide copolymer and a polypropyleneoxide homopolymer, a polyethyleneoxide homopolymer and a polytetramethyleneoxide homopolymer, a polyethyleneoxide copolymer and a polycarbonate homopolymer, a polyethyleneoxide copolymer and a polybutadiene homopolymer, and a polyethyleneoxide copolymer and a polyisobutylene homopolymer.

19. The surface active endgroup-containing polymer of claim 18, wherein the soft segment comprises a blend of a polyethyleneoxide-polytetramethyleneoxide copolymer and polyethyleneoxide homopolymer.

20. The surface active endgroup-containing polymer of claim 19, wherein the soft segment is a blend of a polyethyleneoxide-polytetramethyleneoxide copolymer and a polyethyleneoxide-polypropyleneoxide copolymer.

21. The surface active endgroup-containing polymer of claim 20, wherein the soft segment is a blend of a polyethyleneoxide-polytetramethyleneoxide copolymer and an ethyleneoxide-capped polypropyleneoxide polymer.

22. The surface active endgroup-containing polymer of claim 20, wherein the soft segment is a blend of a polyethyleneoxide-polypropyleneoxide copolymer and a polyethyleneoxide homopolymer.

23. The surface active endgroup-containing polymer of claim 20, wherein the soft segment is a blend of a polyethyleneoxide-polypropyleneoxide copolymer and a polypropyleneoxide homopolymer.

24. The surface active endgroup-containing polymer of claim 20, wherein the soft segment is a blend of a polyethyleneoxide homopolymer and a polytetramethyleneoxide homopolymer providing the copolymer having a lesser tensile strength and elongation in the wet state than in its dry state.

25. The surface active endgroup-containing polymer of claim 20, wherein the soft segment is a blend of a polyethyleneoxide-containing copolymer and a polycarbonate homopolymer.

26. The surface active endgroup-containing polymer of claim 20, wherein the soft segment is a blend of a polyethyleneoxide-containing copolymer and a polybutadiene homopolymer.

27. The surface active endgroup-containing polymer of claim 20, wherein the soft segment is a blend of a polyethyleneoxide-containing copolymer and a polyisobutylene homopolymer.

28. An article formed from the surface active endgroup-containing polymer of claim 1 in the form of a cardiac-assist device, a catheter, a catheter-introducer, a pacemaker lead, a vascular graft, a prosthetic implant, a condom, a condom coating, a glove, or a glove coating.

29. A non-porous, semi-permeable, biocompatible film formed from the surface active endgroup-containing polymer of claim 1.

30. The non-porous film of claim 29, in the form of a flexible sheet or a hollow membrane.

31. The non-porous film of claim 30, being attached to a substrate.

32. The non-porous film of claim 31, in the form of a coating deposited onto said substrate, wherein said substrate is a woven or knitted substrate or a porous polymer.

33. The non-porous film of claim 32, having a thickness of about 1 to 150 microns.

34. The non-porous film of claim 33, having a thickness of about 5 to 150 microns.

35. A surface active endgroup-containing polymer that comprises a linear base polymer having covalently bonded surface active endgroups of a nature and present in an amount such that said polymer has a contact angle hysteresis of the surface that is changed by at least 5% from the contact angle hysteresis of the surface of an otherwise identical polymer that does not contain said covalently bonded surface active endgroups.

36. The surface active endgroup-containing polymer according to claim 35 wherein said polymer has a contact angle hysteresis of the surface that is changed by at least 10% from the contact angle hysteresis of the surface of an otherwise identical polymer that does not contain said covalently bonded surface active endgroups.

37. A segmented block copolymer comprising from about 5 to 45 weight % of at least one hard segment, from about 95 to 55 weight % of at least one soft segment, and from about 0.1 to 15 weight % of at least one surface active endgroup.

38. The segmented block copolymer according to claim 37 wherein said hard segment is selected from the group consisting of a prepolymer of 4,4'-diphenylmethanediisocyanate, ethylenediamine, and 1,3-cyclohexanediamine; a prepolymer of 4,4'-diphenylmethanediisocyanate, ethylenediamine, and 2,2'-bis(hydroxymethyl)propionic acid; a prepolymer of 4,4'-diphenylmethanediisocyanate and butanediol; and 4,4'-diphenylmethanediisocyanate, said soft segment is selected from the group consisting of polytetramethylene oxide, polycarbonate polyol, polyisobutylene, polybutadiene polyol, and a blend of polytetramethylene oxide and polypropylene oxide-polyethylene oxide copolymer, and said surface active endgroup is selected from the group consisting of diethyleneamine, monofunctional OH-terminated polydimethylsiloxane, dodecylamine, fluoroalkyl amine, fluoroalkyl alcohol, a blend of monofunctional OH-terminated polydimethylsiloxane and monofunctional-amine-terminated poly(ethylene oxide), and monofunctional-amine-terminated poly(ethylene oxide).

39. A polymeric composition of matter having the formula

wherein p and q may be the same or different and each is a number from 0 through 1, n is a number from 5 through $10^5$, A is a surface active endgroup, A' is a surface active endgroup different from A, Z is a surface active endgroup that may be the same as one of or different from both of A and A', and z" is a surface active endgroup that is different from Z but may be the same as one of or different from both of A and A', B is a polymer block, C is a polymer block which may be the same as or different from B, and D is a polymer block which may be the same as one of or different from both of B and C.

40. The polymeric composition of matter according to claim 39 having the formula $A[BC]_nZ$ wherein B is a polymeric block selected from the group consisting of polyurethanes, polyureas, polyamides, aromatic polyesters, aromatic polycarbonates, polystyrenes, and polyacrylates, C is a polymeric block selected from the group consisting of polyethers, aliphatic polyesters, polyisoprenes, polybutadienes, polyethylenebutylenes, and aliphatic polycarbonates, A is a polydimethylsiloxane endgroup, and Z is an endgroup selected from the group consisting of polydimethylsiloxanes and poly(ethylene oxides).

41. The polymeric composition of matter according to claim 39 wherein D is the same as C which in turn is the same as B.

42. The polymeric composition of matter according to claim 39 wherein D is the same as B and wherein C is different from B.

43. The polymeric composition of matter according to claim 39 wherein p and q are both 1 and wherein A, B, C, D, and Z are all different from one another.

44. The surface active endgroup-containing polymer according to claim 1 or 37, having the structural formula depicted in FIG. 3.

45. The surface active endgroup-containing polymer according to claim 1 or 37, having the structural formula depicted in FIG. 2.

46. The surface active endgroup-containing polymer according to claim 1 or 37, having the structural formula depicted in FIG. 3.

47. The surface active endgroup-containing polymer according to claim 1 or 37, having the structural formula depicted in FIG. 4.

48. The surface active endgroup-containing polymer according to claim 1 or 37, having the structural formula depicted in FIG. 5.

49. The surface active endgroup-containing polymer according to claim 1 or 37, having the structural formula depicted in FIG. 6.

50. The surface active endgroup-containing polymer according to claim 1 or 37, having the structural formula depicted in FIG. 7.

51. The surface active endgroup-containing polymer according to claim 1 or 37, having the structural formula depicted in FIG. 8.

* * * * *